US009650675B2

(12) United States Patent
Rimseliene et al.

(10) Patent No.: US 9,650,675 B2
(45) Date of Patent: *May 16, 2017

(54) RESTRICTION ENDONUCLEASES AND THEIR USES

(71) Applicant: Thermo Fisher Scientific Baltics UAB, Vilnius (LT)

(72) Inventors: Renata Rimseliene, Vilnius (LT); Remigijus Skirgalia, Vilnius (LT); Arvydas Lubys, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 0 days.

This patent is subject to a terminal disclaimer.

(21) Appl. No.: 14/972,566

(22) Filed: Dec. 17, 2015

(65) Prior Publication Data

US 2016/0194706 A1    Jul. 7, 2016

Related U.S. Application Data

(62) Division of application No. 13/932,365, filed on Jul. 1, 2013, now Pat. No. 9,243,233.

(30) Foreign Application Priority Data

Jul. 5, 2012 (GB) .................................. 1212047.3

(51) Int. Cl.
    *C12Q 1/68*       (2006.01)
    *C12N 9/22*       (2006.01)

(52) U.S. Cl.
    CPC ............. *C12Q 1/6876* (2013.01); *C12N 9/22* (2013.01); *C12Q 1/683* (2013.01); *C12Q 1/6883* (2013.01); *C12Q 2600/154* (2013.01); *C12Q 2600/158* (2013.01)

(58) Field of Classification Search
None
See application file for complete search history.

(56) References Cited

U.S. PATENT DOCUMENTS 9,243,233 B2 *    1/2016    Rimšelien .............. C12Q 1/683

FOREIGN PATENT DOCUMENTS

WO       03/023065 A1     3/2003

OTHER PUBLICATIONS

International Search Report and Written Opinion, PCT/EP2013/063971, mailed Jan. 3, 2014 (10 pages).
Vitkute et al. Specificities of Eleven Different DNA Methyltransferases of Helicobacter pylori Strain 26695. Journal of Bacteriology 183 (2001) 443-450.
EBI Accession No. AFI00542, Helicobacter pylori Shi112 hypothetical protein, Database EMBL, Apr. 20, 2012 (1 page).

(Continued)

*Primary Examiner* — Robert Mondesi
*Assistant Examiner* — Richard Ekstrom
(74) *Attorney, Agent, or Firm* — Thompson Hine LLP

(57) ABSTRACT

A restriction endonuclease with a recognition sequence 5'-TCGA-3'. The restriction endonuclease is sensitive to the presence of a modified cytosine residue in the recognition sequence. Methods and kits using the restriction endonuclease with a recognition sequence 5'-TCGA-3' are also disclosed.

10 Claims, 9 Drawing Sheets

(56) References Cited

OTHER PUBLICATIONS

Slatko et al. Cloning, sequencing and expression of the Taq I restriction—modification system. Nucleic Acids Research 15 (1987) 9781-9796.
UKIPO Search Report for GB App No. 1212047.3, mailed Oct. 30, 2012 (3 pages).
Hypothetical protein HPSH112)01605 [Helicobacter pylori Shi112], NCBI Accession No. AFI00542.1, Apr. 19, 2012.
Kay et al. Evidence for adenine methylation within the mouse myogenic gene Myo-D1. Gene, vol. 151 (1994), pp. 89-95.
Streeck. Single-strand and double strand cleavage at half-modified and fully modified recognition sites for the restriction nucleases Sau3A and Taql. Gene, vol. 12 (1980), pp. 267-275.
Fermentas Products EpiJET™ DNA Methylation Analysis Kit, (2011), available at http://www.fermentas.com/en/products/all/epigenetics/k144-epijet-dna-methylation-kit.
Fermentas Support Technical Reference, Restriction Enzymes: PureExtreme® Quality Guarantee, (2011), available at http://www.fermentas.com/en/support/technical-reference/restriction-enzymes/quality.
Fermentas Products EpiJET™ 5-hmC Analysis Kit Information, (2011), available at http://www.fermentas.com/en/products/all/epigenetics/k1481-epijet-5-hmc-analysis-kit.
Bernstein et al. The Mammalian Epigenome. Cell vol. 128 (2007), pp. 669-681.
Bird. DNA methylation patterns and epigenetic memory. Genes Dev. vol. 16 (2002), pp. 6-21.
Bird. Perceptions of epigenetics. Nature, vol. 447 (2007), pp. 396-398.
Cohen-Karni et al. The MspJI family of modification-dependent restriction endonucleases for epigenetic studies. Proc. Nat. Acad. Sci. U.S.A. vol. 108, No. 27 (2011), pp. 11040-11045.
Colaneri et al. Expanded methyl-sensitive cut counting reveals hypomethylation as an epigenetic state that highlights functional sequences of the genome. Proc. Nat. Acad. Sci. U.S.A. vol. 108, No. 23 (2011), pp. 9715-9720.
Esteller. Epigenetics in Cancer. N. Engl. J. Med. vol. 358, No. 11 (2008), pp. 1148-1159.
Groth et al. Chromatin Challenges during DNA Replication and Repair. Cell, vol. 128 (2007), pp. 721-733.
Hatada et al. Genome-wide profiling of promoter methylation in human. Oncogene, vol. 25 (2006), pp. 3059-3064.
He et al. Tet-mediated formation of 5-carboxylcytosine and its excision by TDG in mammalian DNA. Science. vol. 333, No. 6047 (2011), Abstract.
Holliday and Pugh. DNA Modification Mechanisms and Gene Activity during Development. Science. vol. 187 (1975), pp. 226-232.
Huang et al. Methylation profiling of CpG islands in human breast cancer cells. Hum Mol Genet vol. 8, No. 3 (1999), pp. 459-470.
Khulan et al. Comparative isoschizomer profiling of cytosine methylation: The HELP assay. Genome Res, vol. 16 (2006), pp. 1046-1055.
Koch et al. The landscape of histone modifications across 1% of the human genome in five human cell lines. Genome Res, vol. 17 (2007), pp. 691-707.
Kriaucionis and Heintz. The Nuclear DNA Base 5-Hydroxymethylcytosine Is Present in Purkinje Neurons and the Brain. Science. vol. 324 (2009), pp. 929-930.
Krivtsov et al. H3K79 Methylation Profiles Define Murine and Human MLL-AF4 Leukemias. Cancer Cell, vol. 14 (2007), pp. 355-368.
Mattick and Makunin. Non-coding RNA. Hum Mol Genet, vol. 15, review issue 1 (2006), pp. R17-R29.
Oda et al. High-resolution genome-wide cytosine methylation profiling with simultaneous copy number analysis and optimization for limited cell numbers. Nucleic Acids Res, vol. 37, No. 12 (2009), pp. 3829-3839.
Orlowski and Bujnicki. Structural and evolutionary classification of Type II restriction enzymes based on theoretical and experimental analyses. Nucleic Acids Res. vol. 36, No. 11 (2008), pp. 3552-3569.
Reik. Stability and flexibility of epigenetic gene regulation in mammalian development. Nature, vol. 447 (2007), pp. 425-432.
Riggs. X inactivation, differentiation, and DNA methylation. Cytogenet Cell Genet, vol. 14 (1975), pp. 9-25.
Robertson and Wolffe. Dna Methylation in Health and Disease. Nat Rev Genet, vol. 1 (2000), pp. 11-19.
Suzuki and Bird. DNA methylation landscapes: provocative insights from epigenomics. Nat Rev Genet, vol. 9 (2008), pp. 465-476.
Takamiya et al. The Application of Restriction Landmark Genome Scanning Method for Surveillance of Non-Mendelian Inheritance in $F_1$ Hybrids. Comp. Funct Genomics, vol. 2009, Article ID 245927, 6 pages.
Takata et al. Phenotypic and genotypic variation in methylases involved in type II restriction-modification systems in Helicobacter pylori. Nuc. Acids Res., vol. 30, No. 11 (2009), pp. 2444-2452.
Vikute et al. Specificities of Eleven Different DNA Methyltransferases of Helicobacter pylori Strain 26695. J. Bacteriol, vol. 183 (2001), pp. 443-450.
Weber et al. Chromosome-wide and promoter-specific analyses identify sites of differential DNA methylation in normal and transformed human cells. Nat Genet, vol. 37 (2005), pp. 853-862.
Yan et al. Applications of CpG Island Microarrays for High-Throughput Analysis of DNA Methylation. J. Nutr, vol. 132 pp. 2430S-2434S.
Zheng et al. A unique family of Mrr-like modification-dependent restriction endonucleases. Nucleic Acids Res vol. 38, No. 10 (2010), pp. 5527-5534.
Hypothetical Protein HPSAT_01305 [Helicobacter pylori Sat464], NCBI GenBank Entry: AD005010.1 (Jul. 28, 2011).
Hypothetical Protein HPPN135_01350 [Helicobacter pylori Puno135], NCBI GenBank Entry: AEN17973.1 (Aug. 26, 2011).
Hypothetical Protein KHP_0259 [Helicobacter pylori 51], NCBI GenBank Entry: ACX97473.1 (Oct. 27, 2009).
Hypothetical Protein HPCU_01630 [Helicobacter pylori Cuz20], NCBI GenBank Entry: ADO03503.1 (Jul. 28, 2011).
Hypothetical Protein HPF30_1035 [Helicobacter pylori F30], NCBI GenBank Entry: BAJ57132.1 (Jun. 1, 2011).
Hypothetical Protein HPF32_0270 [Helicobacter pylori F32], NCBI GenBank Entry: BAJ57852.1 (Jun. 1, 2011).
Hypothetical Protein HPKB_0272 [Helicobacter pylori 52], NCBI GenBank Entry: ACX98882.1 (Oct. 27, 2009).
Hypothetical Protein HP9810_1g62 [Helicobacter pylori 98-10], NCBI GenBank Entry: ZP_03438878.1 (Nov. 10, 2010).
Hypothetical Protein HPB128_21 g37 [Helicobacter pylori 8128], NCBI GenBank Entry: ZP_03436984.1 (Nov. 10, 2010).
Hypothetical Protein HPSA_01320 [Helicobacter pylori SouthAfrica7], NCBI GenBank Entry: ADU84288.1 (Jan. 6, 2011).
Hypothetical Protein HPGAM_01475 [Helicobacter pylori Gambia94/24], NCBI GenBank Entry: ADU81143.1 (Jan. 6, 2011).
Hypothetical Protein HPG27 240 [Helicobacter pylori G27], NCBI GenBank Entry: YP_002265873.1 (Sep. 13, 2011).
Hypothetical Protein Hac_1347 [Helicobacter acinonychis str. Sheeba], NCBI GenBank Entry: YP_665084.1 (Jan. 25, 2012).
Hypothetical Protein HPF57 0313 [Helicobacter pylori F57], NCBI GenBank Entry: BAJ59387.1 (Jun. 1, 2011).
Hypothetical Protein HPIN_01175 [Helicobacter pylori India7], NCBI GenBank Entry: ADU79491.1 (Jan. 6, 2011).
Hypothetical Protein HPAG1_0263 [Helicobacter pylori HPAG1], NCBI GenBank Entry: YP_627004.1 (Dec. 17, 2010).
Hypothetical Protein jhp0245 [Helicobacter pylori J99], NCBI GenBank Entry: NP_222966.1 (Jan. 19, 2012).
Unnamed Protein Product [Helicobacter pylori 26695], NCBI GenBank Entry: NP_207059.1 (Jan. 19, 2012).
Conserved Hypothetical Protein [Helicobacter pylori 83], NCBI GenBank Entry: AEE69919.1 (May 11, 2011).
Hypothetical Protein HMPREF9094_0161 [Fusobacterium nucleatum subsp. animalis ATCC 51191], NCBI GenBank Entry: EGQ80805.1 (Jul. 13, 2011).
Conserved Hypothetical Protein [Simonsiella muelleri ATCC 29453], NCBI GenBank Entry: ZP_06753958.1 (Jun. 9, 2010).

(56) References Cited

OTHER PUBLICATIONS

Hypothetical Protein HPF16_0268 [Helicobacter pylori F16], NCBI GenBank Entry: BAJ54865.1 (Jun. 1, 2011).
Hypothetical Protein HPB8_1302 [Helicobacter pylori B8], NCBI GenBank Entry: YP_003729323.1 (Jun. 10, 2013).
Hypothetical Protein HPB128_21g37 [Helicobacter pylori 8128], NCBI GenBank Entry: EEC25275.1 (Dec. 9, 2008).
Conserved Hypothetical Protein [Helicobacter pylori 88], NCBI GenBank Entry: CBI66859.1 (Jun. 15, 2010).
Hypothetical Protein HP9810_1g62 [Helicobacter pylori 98-10], NCBI GenBank Entry: EEC23581.1 (Dec. 9, 2008).
Hypothetical Protein HPG27 240 [Helicobacter pylori G27], NCBI GenBank Entry: ACI27007.1 (May 22, 2012).
Hypothetical Protein Hac_1347 [Helicobacter acinonychis str. Sheeba], NCBI GenBank Entry: CAK00085.1 (Sep. 18, 2009).
Hypothetical Protein HMPREF9021_01113 [Simonsiella muelleri ATCC 29453], NCBI GenBank Entry: EFG30885.1 (Sep. 11, 2012).
NCBI Protein (EMBL) AAA27505 Endonuclease [Thermus aquaticus] Apr. 26, 1993.
REBASE Entry Enzyme Num 3082, TfiTok6AlI, Type II restriction enzyme subtype: P (Jun. 29, 2011).
REBASE Entry Enzyme Num 1808, TflI, Type II restriction enzyme subtype: P (Jun. 29, 2011).
REBASE Entry Enzyme Num 2848, Tsp321, Type II restriction enzyme subtype: P (Jun. 29, 2011).
REBASE Entry Enzyme Num 1831, TthHB8I, Type II restriction enzyme subtype: P (Jun. 29, 2011).
REBASE Entry Enzyme Num 4343, HpyF30I, Type II restriction enzyme subtype: P (Jun. 29, 2011).
REBASE Entry Enzyme Num 1451, PaeR7I, Type II restriction enzyme subtype: P (Jun. 29, 2011).
REBASE Methylation Sensitivity Data for Taql (available as of Jun. 20, 2012).
REBASE Entry Enzyme Num. 4634, EsaBC3I, Type II restriction enzyme subtype: P (Jun. 29, 2011).
REBASE Methylation Sensitivity Data for EsaBC3I (as available on Jun. 20, 2012).
REBASE Methylation Sensitivity Data for Taql (as available on Jun. 20, 2012).
REBASE Similar Restriction Enzymes (Taql) (as available on Apr. 3, 2012).
Fermentas, Certificate of Analysis CpG Methyltransferase (M.SssI), Jul. 2011 (4 pages).
International Preliminary Report on Patentability PCT/EP2013/063971 mailed Jan. 15, 2015 (8 pages).

* cited by examiner

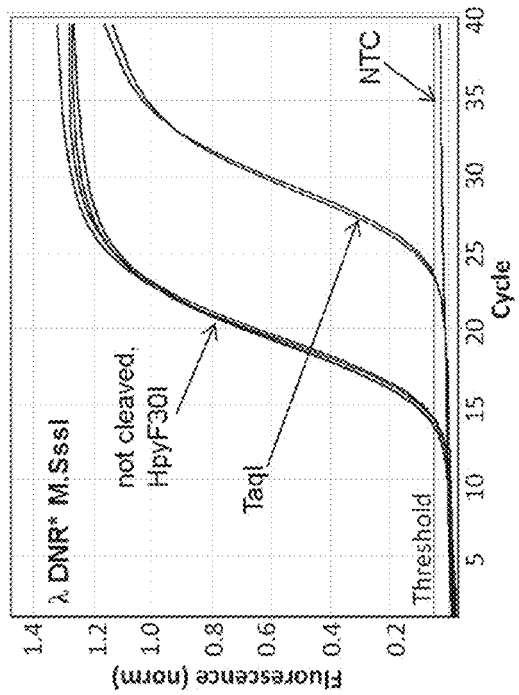
FIGURE 5B
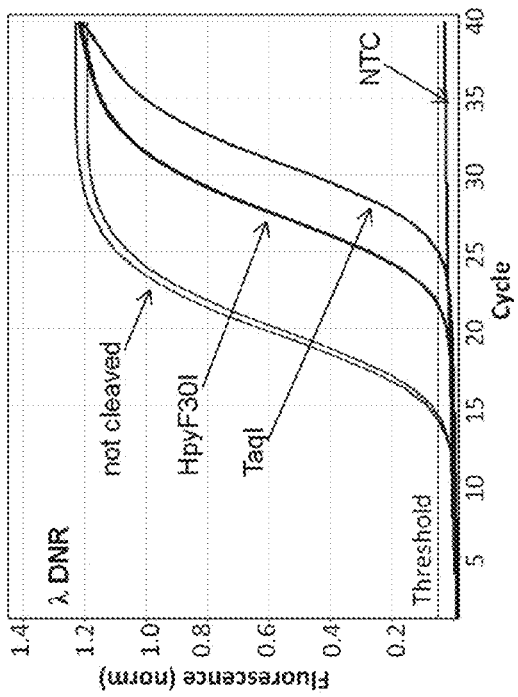
FIGURE 5A
FIGURE 5C
| DNA template | Lambda DNA (5x10⁴ DNA copies) | | Lambda DNA*M.SssI (5x10⁴ DNA copies) | |
|---|---|---|---|---|
| | $C_q$ | Quantity, % | $C_q$ | Quantity, % |
| Not cleaved | 14 | 100 | 14 | 100 |
| HpyF3OI | 21.5 | 0.6 | 14 | 100 |
| TaqI | 25 | 0.06 | 23 | 0.2 |

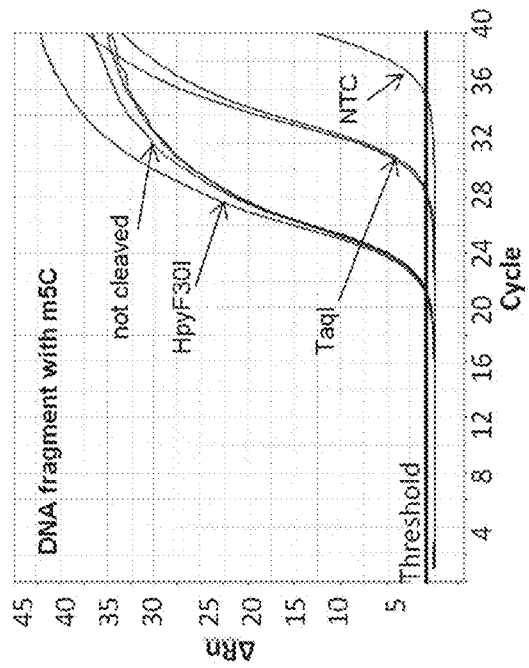
FIGURE 7A
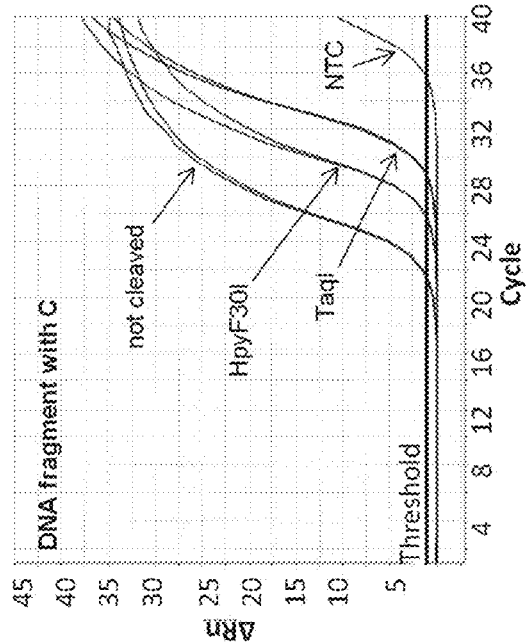
FIGURE 7B
| DNA template | DNA fragment with C (1x10⁴ DNA copies) | | DNA fragment with m5C (1x10⁴ DNA copies) | |
|---|---|---|---|---|
| | $C_q$ | Quantity, % | $C_q$ | Quantity, % |
| Not cleaved | 21.5 | 100 | 21.5 | 100 |
| HpyF30I | 26 | 7 | 21.5 | 100 |
| TaqI | 29 | 0.7 | 29 | 0.7 |
FIGURE 7C

| DNA template | Genomic DNA (3x10⁴ DNA copies) | |
|---|---|---|
| | $C_q$ | Quantity, % |
| Not cleaved | 24.5 | 100 |
| HpyF30I | 30 | 2 |
| PaeR7I | 31.5 | 0.8 |
| TaqI | 32 | 0.7 |

| DNA template | Genomic DNA (3x10$^4$ DNA copies) | |
|---|---|---|
| | C$_q$ | Quantity, % |
| Not cleaved | 24 | 100 |
| HpyF30I | 25 | 50 |
| PaeR7I | 25 | 50 |
| TaqI | 31.5 | 0.8 |

SEQUENCE LISTING

```
<160> NUMBER OF SEQ ID NOS: 37

<210> SEQ ID NO 1
<211> LENGTH: 37
<212> TYPE: DNA
<213> ORGANISM: Artificial Sequence
<220> FEATURE:
<223> OTHER INFORMATION: Primer Tq-hpR-dir

<400> SEQUENCE: 1
gctatttaaa tgcaattttt aaatcaatct ttgggat                              37

<210> SEQ ID NO 2
<211> LENGTH: 34
<212> TYPE: DNA
<213> ORGANISM: Artificial sequence
<220> FEATURE:
<223> OTHER INFORMATION: Primer Tq-hpR-rev

<400> SEQUENCE: 2
atagcggccg cttatgcaag atggttttcc caag                                 34

<210> SEQ ID NO 3
<211> LENGTH: 615
<212> TYPE: DNA
<213> ORGANISM: Helicobacter pylori

<400> SEQUENCE: 3
atgcaatttt taaatcaatc tttgggattt tttaataaag ggcactttga gcccattgac     60
agaaacttca tcacagaaag ctatcaagca ctaaagccga ttgaagaaat tcaaaataaa    120
tacaataaac atgacaacga ttcattttg aatgaattga gagatagcat ggtggctcta    180
tatttagatt atgagcttat caatattcaa aagcatggtc ttgatgccaa aagaagttca    240
agcgatgaat ttttagaaat caaacaagtg tcctttcaaa gtaaaacttg gagcgcgact    300
tttaatgaca ccactttaga aaaagccaaa gttttttgcg atattaaaac gactttagcc    360
gtgggcgttt ggaataatat ttctaatctt ttattcattg tttatggaaa gcaccctgaa    420
```

```
attggcttgt atttagaaca aaaagtaaaa gagtgtcata atgagagcag gcgttcaact    480
caaacgatag gggttagtaa attgatcaaa gaatttgatt ttaaaatgaa acccattgat    540
ttaaaagaac aagagcttat caatcttttt aatcttaaat ttggtcattt ttcttgggaa    600
aaccatcttg cataa                                                    615
```

```
<210> SEQ ID NO 4
<211> LENGTH: 204
<212> TYPE: PRT
<213> ORGANISM: Helicobacter pylori

<400> SEQUENCE: 4
```

```
Met Gln Phe Leu Asn Gln Ser Leu Gly Phe Phe Asn Lys Gly His Phe
1               5                   10                  15

Glu Pro Ile Asp Arg Asn Phe Ile Thr Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Ser
65                  70                  75                  80

Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
        115                 120                 125

Asn Leu Leu Phe Ile Val Tyr Gly Lys His Pro Glu Ile Gly Leu Tyr
    130                 135                 140

Leu Glu Gln Lys Val Lys Glu Cys His Asn Glu Ser Arg Arg Ser Thr
145                 150                 155                 160

Gln Thr Ile Gly Val Ser Lys Leu Ile Lys Glu Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200
```

```
<210> SEQ ID NO 5
<211> LENGTH: 43
<212> TYPE: DNA
<213> ORGANISM: Artificial sequence
<220> FEATURE:
<223> OTHER INFORMATION: Primer Tq-hpM-dir1

<400> SEQUENCE: 5
ctgcagaagg agatttaaat gcataaagtt tttatcatgg aag                     43
```

```
<210> SEQ ID NO 6
<211> LENGTH: 38
<212> TYPE: DNA
<213> ORGANISM: Artificial sequence
<220> FEATURE:
<223> OTHER INFORMATION: Primer Tq-hpM-rev

<400> SEQUENCE: 6
atagcggccg cttatcttaa aatttcgtat tcacttct                           38
```

```
<210> SEQ ID NO 7
<211> LENGTH: 1155
<212> TYPE: DNA
<213> ORGANISM: Helicobacter pylori

<400> SEQUENCE: 7
atgcataaag tttttatcat ggaagctttg gaatgtttga aaagaataga aaagaaagc        60 atccaaacca tctatataga cccccttat aacactaaga gttctaactt tgaatatgaa       120
gacgctcatg ctgactatga aaatggatt gaagaacact tgattttagc aaagtctgtg       180
ttaaaacaaa gcggttgtat ttttatttct atagatgaca ataaaatggc tgaagttaaa       240
atcattgcca atgaaatttt tggaacgcgc aattttttag cacttttat cactaaacaa       300 gccacaaggt ctaacgctaa acacatcaat attacccatg aatatgtttt aagctacgcc       360
aaaaataaag cgttcgctcc tggttttaaa atcttacgaa cgcttttgcc catttatgct       420
aaagcattaa agatttaat gcgaacgatt aaaaatgttt ttagacaaaa aggacaagct       480
caagcccaac ttgtcctaaa agaacaaatc aaagagttat ctaaaaaaga acattttaat       540 ttttaaaaa attataattt ggtggatgaa aaaggtgaaa tttatttcgc taaagattta       600
tctacgcctt cacacccacg cagtgtagcg atacaagaaa tcaatctttt tttagaaccc       660 ttaaaagca gagggtggag cagcgatgaa aagcttaagg atttatatta tcaaaacaga       720
cttattttta agaacaatcg cccttatgaa aaatattacc taaaagaatc gcaagataat       780
tgtttgagcg tgttggattt ttatagccga caaggcacaa agatttaga aaaattaggc       840 ctaaaggggc tttttaagac gccaaaacct gtaggattga ttaaatattt attgttatgc       900 tccacccta aagattctat tattttagat ttttttgcag gcagtgggac aacagcgcaa       960
gcggttatag aagctaatag ggattatgat ttgaattggt cttttttattt tgtgtcaaaaa       1020 gaagaaaaaa ttaaaaataa cccgcaagct gttagcattt taaaaaacaa ggggtatcaa       1080
aacacgattt caaacatcat gctgttgcgt ttagaaaaga tcatcaaaag aagtgaatac       1140
gaaattttaa gataa                                                       1155

<210> SEQ ID NO 8
<211> LENGTH: 384
<212> TYPE: PRT
<213> ORGANISM: Helicobacter pylori

<400> SEQUENCE: 8

Met His Lys Val Phe Ile Met Glu Ala Leu Glu Cys Leu Lys Arg Ile
1               5                   10                  15

Glu Lys Glu Ser Ile Gln Thr Ile Tyr Ile Asp Pro Pro Tyr Asn Thr
            20                  25                  30

Lys Ser Ser Asn Phe Glu Tyr Glu Asp Ala His Ala Asp Tyr Glu Lys
        35                  40                  45

Trp Ile Glu Glu His Leu Ile Leu Ala Lys Ser Val Leu Lys Gln Ser
    50                  55                  60

Gly Cys Ile Phe Ile Ser Ile Asp Asp Asn Lys Met Ala Glu Val Lys
65                  70                  75                  80

Ile Ile Ala Asn Glu Ile Phe Gly Thr Arg Asn Phe Leu Gly Thr Phe
                85                  90                  95

Ile Thr Lys Gln Ala Thr Arg Ser Asn Ala Lys His Ile Asn Ile Thr
            100                 105                 110

His Glu Tyr Val Leu Ser Tyr Ala Lys Asn Lys Ala Phe Ala Pro Gly
        115                 120                 125
```

-continued

```
Phe Lys Ile Leu Arg Thr Leu Leu Pro Ile Tyr Ala Lys Ala Leu Lys
        130                 135                 140

Asp Leu Met Arg Thr Ile Lys Asn Val Phe Arg Gln Lys Gly Gln Ala
145                 150                 155                 160

Gln Ala Gln Leu Val Leu Lys Glu Gln Ile Lys Glu Leu Ser Lys Lys
                165                 170                 175

Glu His Phe Asn Phe Leu Lys Asn Tyr Asn Leu Val Asp Glu Lys Gly
            180                 185                 190

Glu Ile Tyr Phe Ala Lys Asp Leu Ser Thr Pro Ser His Pro Arg Ser
        195                 200                 205

Val Ala Ile Gln Glu Ile Asn Leu Phe Leu Gly Pro Leu Lys Ser Arg
210                 215                 220

Gly Trp Ser Ser Asp Glu Lys Leu Lys Asp Leu Tyr Tyr Gln Asn Arg
225                 230                 235                 240

Leu Ile Phe Lys Asn Asn Arg Pro Tyr Glu Lys Tyr Tyr Leu Lys Glu
                245                 250                 255

Ser Gln Asp Asn Cys Leu Ser Val Leu Asp Phe Tyr Ser Arg Gln Gly
            260                 265                 270

Thr Lys Asp Leu Glu Lys Leu Gly Leu Lys Gly Leu Phe Lys Thr Pro
        275                 280                 285

Lys Pro Val Gly Leu Ile Lys Tyr Leu Leu Leu Cys Ser Thr Pro Lys
290                 295                 300

Asp Ser Ile Ile Leu Asp Phe Phe Ala Gly Ser Gly Thr Thr Ala Gln
305                 310                 315                 320

Ala Val Ile Glu Ala Asn Arg Asp Tyr Asp Leu Asn Trp Ser Phe Tyr
                325                 330                 335

Leu Cys Gln Lys Glu Lys Ile Lys Asn Asn Pro Gln Ala Val Ser
            340                 345                 350

Ile Leu Lys Asn Lys Gly Tyr Gln Asn Thr Ile Ser Asn Ile Met Leu
        355                 360                 365

Leu Arg Leu Glu Lys Ile Ile Lys Arg Ser Glu Tyr Glu Ile Leu Arg
370                 375                 380
```

<210> SEQ ID NO 9
<211> LENGTH: 55
<212> TYPE: DNA
<213> ORGANISM: Artificial sequence
<220> FEATURE:
<223> OTHER INFORMATION: Synthetic Oligonucleotide

<400> SEQUENCE: 9
agcactctag aggatccccg ggtaccgagc tcgaattcac tggccgtcgt tttac         55

<210> SEQ ID NO 10
<211> LENGTH: 55
<212> TYPE: DNA
<213> ORGANISM: Artificial sequence
<220> FEATURE:
<223> OTHER INFORMATION: Synthetic Oligonucleotide

<400> SEQUENCE: 10
gtaaaacgac ggccagtgaa ttcgagctcg gtacccgggg atcctctaga gtgct         55

<210> SEQ ID NO 11
<211> LENGTH: 204
<212> TYPE: PRT
<213> ORGANISM: Helicobacter pylori

<400> SEQUENCE: 11

```
Met Gln Phe Leu Asn Gln Ser Leu Gly Phe Asn Lys Gly His Phe
1               5                   10                  15

Glu Pro Ile Asp Arg Asn Phe Ile Thr Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Ser
65                  70                  75                  80

Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
        115                 120                 125

Asn Leu Leu Phe Ile Val Tyr Gly Lys His Pro Lys Ile Gly Leu Tyr
    130                 135                 140

Leu Glu Gln Lys Val Lys Glu Cys His Asn Glu Ser Arg Arg Ser Thr
145                 150                 155                 160

Gln Thr Ile Gly Val Ser Lys Leu Ile Lys Lys Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200
```

<210> SEQ ID NO 12
<211> LENGTH: 204
<212> TYPE: PRT
<213> ORGANISM: Helicobacter pylori

<400> SEQUENCE: 12

```
Met Gln Phe Leu Asn Gln Ser Leu Gly Phe Asn Lys Gly His Phe
1               5                   10                  15

Lys Pro Ile Asp Arg Asn Phe Ile Thr Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Ser
65                  70                  75                  80

Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
        115                 120                 125

Asn Leu Leu Phe Ile Val Tyr Gly Lys His Pro Lys Ile Gly Leu Tyr
    130                 135                 140

Leu Glu Gln Lys Ala Lys Glu Cys His Asn Glu Ser Arg Arg Ser Thr
145                 150                 155                 160
```

Gln Thr Ile Gly Val Ser Lys Leu Ile Lys Glu Phe Asp Phe Lys Met
                    165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200

<210> SEQ ID NO 13
<211> LENGTH: 204
<212> TYPE: PRT
<213> ORGANISM: Helicobacter pylori

<400> SEQUENCE: 13

Met Gln Phe Leu Asn Gln Ser Leu Gly Phe Phe Asn Lys Gly His Phe
1               5                   10                  15

Glu Pro Ile Asp Arg Asn Phe Ile Ala Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Leu
65                  70                  75                  80

Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
        115                 120                 125

Asn Leu Leu Phe Ile Val Tyr Gly Lys His Pro Lys Ile Gly Leu Tyr
    130                 135                 140

Leu Glu Gln Lys Val Lys Glu Cys His Asn Glu Ser Arg Arg Ser Thr
145                 150                 155                 160

Gln Thr Ile Gly Val Ser Lys Leu Ile Lys Glu Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200

<210> SEQ ID NO 14
<211> LENGTH: 204
<212> TYPE: PRT
<213> ORGANISM: Helicobacter pylori

<400> SEQUENCE: 14

Met Gln Phe Leu Asn Gln Ser Leu Gly Phe Phe Asn Lys Gly His Phe
1               5                   10                  15

Glu Pro Ile Asp Arg Asn Phe Ile Thr Glu Ser Tyr Gln Ala Leu Lys
            20                  25                  30

Ser Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Asn Ser
65                  70                  75                  80

```
Ser Asp Glu Phe Leu Glu Ile Lys Gln Val Ser Phe Gln Ser Lys Thr
            85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Lys Ile Gly Leu Tyr
            130                 135                 140

Leu Glu Gln Lys Val Lys Glu Cys His Asn Glu Ser Arg Arg Ser Thr
145                 150                 155                 160

Gln Thr Ile Gly Val Ser Lys Leu Ile Lys Glu Phe Asp Phe Lys Met
            165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
            195                 200

<210> SEQ ID NO 15
<211> LENGTH: 204
<212> TYPE: PRT
<213> ORGANISM: Helicobacter pylori

<400> SEQUENCE: 15

Met Gln Phe Leu Asn Gln Ser Leu Gly Phe Asn Lys Gly His Phe
1               5                   10                  15

Glu Pro Ile Asp Arg Thr Phe Ile Thr Glu Ser Tyr Gln Ala Leu Lys
            20                  25                  30

Pro Ile Glu Lys Ile Gln Asn Lys Tyr Asn Lys His Asp Asn Asp Ser
            35                  40                  45

Phe Leu Asn Glu Leu Arg Asp Ser Met Val Ala Leu Tyr Leu Asp Tyr
            50                  55                  60

Glu Leu Ile Asn Ile Gln Lys His Gly Leu Asp Ala Thr Arg Ser Ser
65                  70                  75                  80

Ser Asp Glu Phe Leu Glu Ile Lys Gln Val Ser Phe Gln Ser Lys Thr
            85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Lys Ile Gly Leu Tyr
            130                 135                 140

Leu Glu Gln Lys Val Lys Glu Cys His Asn Glu Ser Arg Arg Ser Thr
145                 150                 155                 160

Gln Thr Ile Gly Val Ser Lys Leu Ile Lys Glu Phe Asp Phe Lys Met
            165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
            195                 200

<210> SEQ ID NO 16
<211> LENGTH: 204
<212> TYPE: PRT
<213> ORGANISM: Helicobacter pylori
```

<400> SEQUENCE: 16

Met Arg Phe Leu Asn Gln Ser Leu Gly Phe Asn Lys Gly Cys Phe
1               5                   10                  15

Glu Pro Ile Asp Arg Asn Phe Ile Ala Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Ser
65                  70                  75                  80

Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
                100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Lys Ile Gly Leu Tyr
        130                 135                 140

Leu Glu Gln Lys Val Lys Glu Cys His Asn Glu Ser Arg Arg Ser Thr
145                 150                 155                 160

Gln Thr Ile Gly Ile Ser Lys Leu Ile Lys Glu Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200

<210> SEQ ID NO 17
<211> LENGTH: 204
<212> TYPE: PRT
<213> ORGANISM: Helicobacter pylori

<400> SEQUENCE: 17

Met Arg Phe Leu Asn Gln Ser Leu Gly Phe Phe Asn Lys Gly Arg Phe
1               5                   10                  15

Glu Pro Ile Asp Arg Asn Phe Ile Thr Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Ser
65                  70                  75                  80

Ser Asp Glu Phe Leu Glu Thr Lys Gln Val Ser Phe Gln Ser Lys Thr
                85                  90                  95

Trp Ser Ala Thr Phe Asn Asp Thr Thr Leu Glu Lys Ala Lys Val Phe
                100                 105                 110

Cys Asp Val Lys Thr Thr Leu Ala Val Gly Val Trp Asn Asn Ile Ser
            115                 120                 125

Asn Leu Leu Phe Ile Val Tyr Gly Lys His Pro Glu Ile Val Leu Tyr
        130                 135                 140

Leu Glu Gln Lys Val Lys Glu Cys His Asn Glu Ser Arg Arg Ser Thr
145                 150                 155                 160

```
Gln Thr Ile Gly Val Ser Lys Leu Ile Lys Glu Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200

<210> SEQ ID NO 18
<211> LENGTH: 204
<212> TYPE: PRT
<213> ORGANISM: Helicobacter pylori

<400> SEQUENCE: 18

Met Gln Phe Leu Asn Gln Ser Leu Gly Phe Phe Asn Lys Gly His Phe
1               5                   10                  15

Glu Pro Ile Asp Arg Asn Phe Ile Ala Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asn Ser Ile Val Ala Leu Tyr Leu Asp Tyr
    50                  55                  60

Glu Leu Ile Asn Ile Gln Lys His Gly Leu Asp Ala Lys Arg Ser Ser
65                  70                  75                  80

Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
        115                 120                 125

Asn Leu Leu Phe Ile Val Tyr Gly Lys His Pro Lys Ile Gly Leu Tyr
    130                 135                 140

Leu Glu Gln Lys Val Lys Glu Cys His Asn Glu Ser Arg His Ser Thr
145                 150                 155                 160

Gln Thr Ile Gly Val Ser Lys Leu Thr Lys Glu Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser Trp Glu Asn His Leu Ala
        195                 200

<210> SEQ ID NO 19
<211> LENGTH: 198
<212> TYPE: PRT
<213> ORGANISM: Helicobacter pylori

<400> SEQUENCE: 19

Met Gln Phe Leu Asn Gln Ser Leu Gly Phe Phe Asn Lys Gly Cys Phe
1               5                   10                  15

Glu Pro Ile Asp Arg Asn Phe Ile Thr Glu Ser Tyr Gln Ala Leu Lys
            20                  25                  30

Pro Ile Glu Glu Ile Gln Asn Lys Tyr Asn Lys His Asp Asn Asp Ser
        35                  40                  45

Phe Leu Asn Glu Leu Arg Asp Ser Met Val Ala Leu Tyr Leu Asp Tyr
    50                  55                  60

Glu Leu Ile Asn Ile Gln Lys His Gly Leu Asp Ala Lys Arg Ser Ser
65                  70                  75                  80
```

```
Ser Asp Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Glu Ile Gly Leu Tyr
            130                 135                 140

Leu Glu Gln Lys Val Lys Glu Cys His Asn Glu Ser Arg Arg Ser Thr
145                 150                 155                 160

Gln Thr Ile Gly Val Ser Lys Leu Ile Lys Glu Phe Asp Phe Lys Met
                165                 170                 175

Lys Pro Ile Asp Leu Lys Glu Gln Glu Leu Ile Asn Leu Phe Asn Leu
            180                 185                 190

Lys Phe Gly His Phe Ser
            195
```

<210> SEQ ID NO 20
<211> LENGTH: 204
<212> TYPE: PRT
<213> ORGANISM: Helicobacter pylori

<400> SEQUENCE: 20

```
Met Gln Phe Leu Asn Gln Ser Leu Gly Phe Asn Lys Gly Cys Phe
1               5                   10                  15

Glu Pro Ile Asp Arg Asn Phe Ile Thr Glu Ser Tyr Gln Ala Leu Lys
                20                  25                  30

Pro Ile Glu Lys Ile Gln Asn Lys Tyr Asn Lys His Asp Asn Asp Ser
            35                  40                  45

Phe Leu Asn Glu Leu Arg Asp Ser Met Val Ala Leu Tyr Leu Asp Tyr
        50                  55                  60

Glu Leu Ile Asn Thr Gln Lys His Gly Leu Asp Ala Lys Arg Ser Ser
65                  70                  75                  80

Ser Asp Glu Phe Leu Glu Ile Lys Gln Val Phe Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Glu Met Gly Leu Tyr
            130                 135                 140

Leu Glu Gln Lys Val Lys Glu Cys His Asn Glu Ser Arg Arg Ser Thr
145                 150                 155                 160

Gln Thr Ile Gly Ile Ser Lys Leu Ile Lys Glu Phe Asp Phe Lys Met
                165                 170                 175

Lys Pro Ile Asp Ser Lys Glu Gln Glu Leu Ile Asn Leu Phe Asn Leu
            180                 185                 190

Lys Phe Gly Arg Phe Ser Trp Glu Asn Tyr Leu Ala
            195                 200
```

<210> SEQ ID NO 21
<211> LENGTH: 204
<212> TYPE: PRT
<213> ORGANISM: Helicobacter pylori

<400> SEQUENCE: 21

```
Met Gln Phe Leu Asn Gln Ser Leu Gly Phe Asn Lys Gly Cys Phe
 1               5                  10                  15

Glu Pro Ile Asp Arg Asn Phe Ile Thr Glu Ser Tyr Gln Ala Leu Lys
             20                  25                  30

Pro Ile Glu Glu Ile Gln Asn Lys Tyr Asn Lys His Asp Asn Asp Ser
         35                  40                  45

Phe Leu Asn Glu Leu Arg Asp Ser Met Val Ala Leu Tyr Leu Asp Tyr
     50                  55                  60

Asn Leu Ile Asn Thr Gln Lys His Gly Leu Asp Ala Lys Arg Ser Ser
 65                  70                  75                  80

Ser Asp Glu Phe Leu Glu Ile Lys Gln Val Ser Phe Gln Ser Lys Thr
                 85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Glu Met Gly Leu Tyr
        130                 135                 140

Leu Glu Gln Lys Val Lys Glu Cys His Asn Glu Ser Arg Arg Ser Thr
145                 150                 155                 160

Gln Thr Ile Gly Ile Ser Lys Leu Ile Lys Glu Phe Glu Phe Lys Met
                165                 170                 175

Lys Pro Ile Asp Ser Lys Glu Gln Glu Leu Ile Asn Leu Phe Asn Leu
            180                 185                 190

Lys Phe Gly Arg Phe Ser Trp Glu Asn Cys Leu Ala
        195                 200
```

<210> SEQ ID NO 22
<211> LENGTH: 204
<212> TYPE: PRT
<213> ORGANISM: Helicobacter pylori

<400> SEQUENCE: 22

```
Met Gln Phe Leu Asn Gln Ser Leu Gly Phe Asn Lys Gly Cys Phe
 1               5                  10                  15

Glu Pro Ile Asp Arg Asn Phe Ile Thr Glu Ser Tyr Gln Ala Leu Lys
             20                  25                  30

Pro Ile Glu Glu Ile Gln Asn Lys Tyr Asn Lys His Asp Asn Asp Ser
         35                  40                  45

Phe Leu Asn Glu Leu Arg Asp Ser Met Val Ala Leu Tyr Leu Asp Tyr
     50                  55                  60

Asp Leu Ile Asn Thr Gln Lys His Gly Leu Asp Ala Lys Arg Ser Ser
 65                  70                  75                  80

Asn Asp Glu Phe Leu Glu Ile Lys Gln Val Ser Phe Gln Ser Lys Thr
                 85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
            115                 120                 125

Asn Leu Leu Phe Ile Val Tyr Gly Lys His Pro Glu Met Gly Leu Tyr
        130                 135                 140

Leu Glu Gln Lys Val Lys Glu Cys His Asn Glu Arg Arg Arg Ser Thr
145                 150                 155                 160
```

```
Gln Thr Ile Gly Ile Ser Lys Leu Ile Lys Glu Phe Asp Ser Lys Met
                165                 170                 175

Lys Pro Ile Asp Ser Lys Glu Gln Glu Leu Ile Asn Leu Phe Asn Leu
            180                 185                 190

Lys Phe Gly Arg Phe Ser Trp Glu Asn Tyr Leu Ala
        195                 200
```

<210> SEQ ID NO 23
<211> LENGTH: 204
<212> TYPE: PRT
<213> ORGANISM: Helicobacter acinonychis

<400> SEQUENCE: 23

```
Met Gln Phe Leu Asn Gln Ser Leu Asp Phe Phe Asn Lys Gly Cys Phe
1               5                   10                  15

Glu Pro Ile Asp Arg Asn Phe Ile Thr Glu Ser Cys Gln Ala Leu Lys
            20                  25                  30

Pro Ile Glu Lys Ile Gln Asn Lys Tyr Asn Lys His Asp Asn Asp Ser
        35                  40                  45

Phe Phe Asn Glu Leu Arg Asp Ser Met Val Ala Leu Phe Leu Asp Tyr
    50                  55                  60

Asp Leu Ile Asn Thr Gln Lys His Gly Leu Asp Ala Lys Lys Val Gln
65                  70                  75                  80

Gly Asn Glu Phe Leu Glu Ile Lys Gln Val Ser Phe Gln Ser Lys Thr
                85                  90                  95

Trp Ser Ala Thr Phe Asn Asp Thr Thr Leu Glu Lys Ala Lys Val Phe
            100                 105                 110

Cys Asp Ile Lys Thr Thr Leu Ala Val Gly Val Trp Asn Asn Ile Ser
        115                 120                 125

Asn Leu Leu Phe Ile Val Tyr Gly Lys His Pro Glu Ile Gly Leu Tyr
    130                 135                 140

Leu Glu Gln Lys Val Lys Glu Cys His Asn Gly Ser Arg Arg Ser Thr
145                 150                 155                 160

Gln Thr Ile Gly Ile Ser Lys Leu Ile Lys Glu Phe Ser Phe Lys Met
                165                 170                 175

Lys Pro Ile Asp Leu Lys Glu Gln Glu Leu Ile Asn Leu Phe Lys Leu
            180                 185                 190

Lys Phe Gly Asn Phe Ser Trp Gly Asn Tyr Leu Ala
        195                 200
```

<210> SEQ ID NO 24
<211> LENGTH: 216
<212> TYPE: PRT
<213> ORGANISM: Fusobacterium nucleatum

<400> SEQUENCE: 24

```
Met Trp Glu Asn Arg Glu Glu Lys Lys Met Phe Lys Asn Gln Asn Leu
1               5                   10                  15

Pro Leu Phe Asn Lys Gly Thr Tyr Lys Glu Ile Asp Arg Val Tyr Val
            20                  25                  30

Ser Arg Val Gln Asn Ala Met Phe Gln Val Met Glu Leu Gln Glu Glu
        35                  40                  45

Tyr Gly Lys Tyr Asp Asn Asp Ser Phe Leu Asn Glu Met Lys Asp Ser
    50                  55                  60

Met Val Gly Met Tyr Leu Gly Tyr Glu Phe Val Asn Ile Asp Lys His
65                  70                  75                  80
```

```
Gly Phe Asp Ala Lys Arg Lys Ser Asn Lys Tyr Asp Glu Trp Leu Glu
            85                  90                  95

Val Lys Gln Val Ser Phe Lys Ser Glu Ser Trp Gln Ala Thr Phe Asn
        100                 105                 110

Asp Thr Thr Ile Glu Lys Ala Glu Ala Phe Lys Asp Ile Lys Leu Asn
            115                 120                 125

Leu Ala Val Gly Val Trp Asn Lys Met Met Glu Leu Met Phe Ile Val
130                 135                 140

Tyr Gly Lys Asn Tyr Glu Ile Gly Glu Tyr Leu Glu Lys Met Val Ile
145                 150                 155                 160

Lys Cys Lys Glu Glu Arg Arg Ser Thr Gln Thr Ile Ser Val Gln
                165                 170                 175

Ser Leu Ile Glu Asn Tyr Asn Phe Arg Val Lys Pro Val Asn Asn Ser
            180                 185                 190

Ser Lys Glu Val Glu Leu Leu Lys Ile Arg Phe Lys Lys Tyr Asn
        195                 200                 205

Trp Arg Asp Arg Ile Asp Lys Glu
210                 215

<210> SEQ ID NO 25
<211> LENGTH: 212
<212> TYPE: PRT
<213> ORGANISM: Simonsiella muelleri

<400> SEQUENCE: 25

Met Thr Glu Gln Val Phe Phe Lys Asn Gln Asp Leu Lys Ile Phe His
1               5                   10                  15

Lys Gly Asn Tyr Gln Glu Ile Asn Arg Asp Phe Ile Ser Glu Ala Asn
            20                  25                  30

His Ala Ile Lys Pro Leu Asn Val Ile Gln Lys Tyr Lys Lys Leu
        35                  40                  45

Asp Asn Asp Thr Phe Phe Asn Glu Leu Arg Asp Gly Met Ile Gly Ala
50                  55                  60

Tyr Leu Gly Tyr Asp Leu Val Asn Ile Glu Lys His Gly Leu Asp Ala
65                  70                  75                  80

Lys Asn Ser Glu Asn Asn Gln Phe Leu Glu Val Lys Gln Ala Ser Phe
            85                  90                  95

Ser Ala Lys Ser Trp Val Ala Thr Phe Asn Asp Thr Thr Tyr Glu Lys
        100                 105                 110

Ala Glu Ala Phe Glu Asp Glu Lys Leu Phe Leu Ala Val Gly Val Trp
        115                 120                 125

Ala Gly Leu Ser Glu Leu Leu Phe Ile Val Tyr Gly Gln Asn Pro Leu
130                 135                 140

Ile Gly Gln Tyr Leu Lys Ser Arg Val Asp Ile Phe Lys Ser Gly Gly
145                 150                 155                 160

Ser Val Arg Ser Thr Gln Ser Ile Thr Ile Lys Asp Leu Val Val Cys
                165                 170                 175

Tyr Gly Phe Lys Ile Leu Phe Pro Thr Gln Arg Lys Glu Ile Lys
        180                 185                 190

Asn Ile Phe Arg Leu Lys Tyr Lys Gly Glu Asp Trp Trp Ser Gly Ala
            195                 200                 205

Phe Val Asp Glu
210
```

<210> SEQ ID NO 26
<211> LENGTH: 263
<212> TYPE: PRT
<213> ORGANISM: Thermus aquaticus

<400> SEQUENCE: 26

Met Ala Ser Thr Gln Ala Gln Lys Ala Leu Glu Thr Phe Glu Arg Phe
1               5                   10                  15

Leu Ala Ser Leu Asp Leu Glu Ser Tyr Gln Gln Lys Tyr Arg Pro Ile
            20                  25                  30

Lys Thr Val Glu Gln Asp Leu Pro Arg Glu Leu Asn Pro Leu Pro Asp
        35                  40                  45

Leu Tyr Glu His Tyr Trp Lys Ala Leu Glu Asp Asn Pro Ser Phe Leu
    50                  55                  60

Gly Phe Glu Glu Phe Asp His Trp Trp Glu Lys Arg Leu Arg Pro
65                  70                  75                  80

Leu Asp Glu Phe Ile Arg Lys Tyr Phe Trp Gly Cys Ser Tyr Ala Phe
                85                  90                  95

Val Arg Leu Gly Leu Glu Ala Arg Leu Tyr Arg Thr Ala Val Ser Ile
            100                 105                 110

Trp Thr Gln Phe His Phe Cys Tyr Arg Trp Asn Ala Ser Cys Glu Leu
        115                 120                 125

Pro Leu Glu Ala Ala Pro Glu Leu Asp Ala Gln Gly Ile Asp Ala Leu
    130                 135                 140

Ile His Thr Ser Gly Ser Ser Thr Gly Ile Gln Ile Lys Lys Glu Thr
145                 150                 155                 160

Tyr Arg Ser Glu Ala Lys Ser Glu Asn Arg Phe Leu Arg Lys Gln Arg
                165                 170                 175

Gly Thr Ala Leu Ile Glu Ile Pro Tyr Thr Leu Gln Thr Pro Glu Glu
            180                 185                 190

Leu Glu Glu Lys Ala Lys Arg Ala Arg Val Asn Gly Glu Thr Tyr Arg
        195                 200                 205

Leu Trp Ala Lys Val Ala His His Leu Asp Arg Leu Glu Asn Gly Phe
    210                 215                 220

Val Ile Phe Arg Glu Ser Tyr Val Lys Ser Ile Glu Leu Phe Leu Gln
225                 230                 235                 240

Lys Asn Ala Pro Thr Leu Ser Gly Leu Ile Arg Trp Asp Arg Val Ala
                245                 250                 255

Gln Glu Ala Leu Thr Ala Pro
            260

<210> SEQ ID NO 27
<211> LENGTH: 22
<212> TYPE: DNA
<213> ORGANISM: Artificial Sequence
<220> FEATURE:
<223> OTHER INFORMATION: Primer Lambda_fw

<400> SEQUENCE: 27
ctgattcgtg gaacagatac tc                                           22

<210> SEQ ID NO 28
<211> LENGTH: 21
<212> TYPE: DNA
<213> ORGANISM: Artificial Sequence
<220> FEATURE:
<223> OTHER INFORMATION: Primer Lambda_rw

```
<400> SEQUENCE: 28
acacttcagg agtggaacgc a                                          21

<210> SEQ ID NO 29
<211> LENGTH: 20
<212> TYPE: DNA
<213> ORGANISM: Artificial Sequence
<220> FEATURE:
<223> OTHER INFORMATION: Primer DAPK_Tq_fw1

<400> SEQUENCE: 29
cttttgcttt cccagccagg                                            20

<210> SEQ ID NO 30
<211> LENGTH: 20
<212> TYPE: DNA
<213> ORGANISM: Artificial Sequence
<220> FEATURE:
<223> OTHER INFORMATION: Primer DAPK_Tq_rw1

<400> SEQUENCE: 30
gatcgcactt ctccccgaag                                            20

<210> SEQ ID NO 31
<211> LENGTH: 20
<212> TYPE: DNA
<213> ORGANISM: Artificial Sequence
<220> FEATURE:
<223> OTHER INFORMATION: Primer Rasf_fw2

<400> SEQUENCE: 31
aagatcacgg tccagcctct                                            20

<210> SEQ ID NO 32
<211> LENGTH: 19
<212> TYPE: DNA
<213> ORGANISM: Artificial Sequence
<220> FEATURE:
<223> OTHER INFORMATION: Primer Rasf_rev2

<400> SEQUENCE: 32
gcaacacact tggcctacc                                             19

<210> SEQ ID NO 33
<211> LENGTH: 25
<212> TYPE: DNA
<213> ORGANISM: Artificial Sequence
<220> FEATURE:
<223> OTHER INFORMATION: Primer konv_dir

<400> SEQUENCE: 33
aaatacaccc ctaaacctca aaatc                                      25

<210> SEQ ID NO 34
<211> LENGTH: 25
<212> TYPE: DNA
<213> ORGANISM: Artificial Sequence
<220> FEATURE:
<223> OTHER INFORMATION: Primer konv_rev

<400> SEQUENCE: 34
atatttggtt tatttattgg gtggg                                      25
```

```
<210> SEQ ID NO 35
<211> LENGTH: 24
<212> TYPE: DNA
<213> ORGANISM: Artificial Sequence
<220> FEATURE:
<223> OTHER INFORMATION: M13/pUC reverse sequencing primer

<400> SEQUENCE: 35
gagcggataa caatttcaca cagg                                          24

<210> SEQ ID NO 36
<211> LENGTH: 23
<212> TYPE: DNA
<213> ORGANISM: Artificial Sequence
<220> FEATURE:
<223> OTHER INFORMATION: Primer X174_for

<400> SEQUENCE: 36
cacgccagaa tacgaaagac cag                                           23

<210> SEQ ID NO 37
<211> LENGTH: 24
<212> TYPE: DNA
<213> ORGANISM: Artificial Sequence
<220> FEATURE:
<223> OTHER INFORMATION: X174_rev

<400> SEQUENCE: 37
cgataaacca accatcagca tgag                                          24
```

RESTRICTION ENDONUCLEASES AND THEIR USES

This application is a Divisional application of U.S. Ser. No. 13/932,365, filed Jul. 1, 2013, which claims priority from co-pending Great Britain Application Serial No. GB1212047.3 filed Jul. 5, 2012, each of which is expressly incorporated by reference herein in its entirety.

FIELD OF INVENTION

The invention relates to cytosine modification sensitive, in one embodiment cytosine methylation sensitive, restriction endonucleases and their uses alone or in combination with other restriction endonucleases, e.g., TaqI, and to methods of analysis of cytosine modification in the context of 5'-TCGA-3' nucleotide sequence.

BACKGROUND

The term epigenetics is used to define heritable changes in gene regulation or cellular phenotype that occur without alteration in DNA sequence (Bird 2007). Epigenetic analysis could help explain why cells with identical genotype could have different phenotype. Thus epigenetics is considered to be the missing chain between genotype and phenotype (Bemstein et al. 2007; Reik 2007).

The genetic material in eukaryotic cells exists as nucleic acids and protein complex, termed chromatin. The basic unit of chromatin is the nucleosome, which is composed of DNA wrapped around the octamer of histone proteins. Nucleosomes are then packed into higher-order structures and finally form chromosomes. Based on the state of condensation chromatin is identified as euchromatin (less condensed, and containing most actively transcribed genes) or heterochromatin (highly condensed and the transcriptionally silent form of chromatin). In general, epigenetic modifications regulate gene expression level through the change in chromatin condensation state. DNA methylation usually suppresses gene transcription as it induces binding of regulating proteins, which promote chromatin condensation. Histone modifications (methylation, acetylation, phosphorylation, ubiquitylation, and sumoylation) also regulate chromatin structure and affect DNA transcription, replication, repair and recombination (Groth et al. 2007; Koch et al. 2007; Krivtsov et al. 2008). For example histone acetylation favors euchromatin formation as it impairs the DNA-histone interaction and promotes chromatin decondensation. Small and non-coding RNAs can also regulate chromatin condensation, gene transcription, and thus are also recognized as epigenetic markers (Mattick and Makunin 2006).

DNA methylation is the most popular and widely analyzed epigenetic modification, known since 1975 (Holliday and Pugh 1975; Riggs 1975). DNA in mammalian genomes is primarily methylated at CpG sites. Most of CpG sites are located in so called CpG islands. CpG islands are described as 0.5 kb-5 kb long, GC rich (>60%) genome regions with a high frequency of CpG dinucleotides. CpG islands are usually located in the vicinity of promoters or the first exons of the genes. Methylation in CpG islands usually results in transcription inactivation and gene silencing (Robertson and Wolffe 2000).

5-methyl cytosine (m5C) is the most abundant DNA modification in the mammalian genome. Often m5C is called the fifth base of DNA. Methylation of cytosine in mammals occurs within CpG sites and is catalyzed by DNA methyltransferases. De novo methylation of CpG dinucleotides is performed by DNMT3a and DNMT3b DNA methyltranferases. DNMT1 DNA methyltransferase maintains the DNA methylation pattern during the DNA replication cycle (Bird 2002). In addition to 5-methyl cytosine (m5C), one more cytosine modification, 5-hydroxymethyl cytosine (hm5C), was discovered recently in mouse brain cells (Kriaucionis and Heintz 2009). The biological significance of hm5C is still under investigation. However it is hypothesized that hm5C participates in DNA demethylation processes and regulation of gene transcription.

The most popular technique used for DNA methylation analysis is bisulfiite treatment. This process deaminates all unmodified cytosines into uracils, while m5C and hm5C are resistant to this type of conversion. During bisulfiite treatment cytosines in the target sequence are changed to uracil if they are umethylated, or remain unchanged if they are methylated. Changes in DNA sequence can further be detected using molecular biology techniques such as DNA sequencing, PCR, qPCR, restriction analysis, Southern blotting, primer extension, HPLC, and MALDI-TOF MS etc. (Esteller 2008; Suzuki and Bird 2008).

Along with bisulfite analysis, DNA methylation status can be interrogated using different restriction endonucleases, whose cleavage of DNA at particular target sequences can be either blocked (Colaneri et al. 2011) or induced (Zheng et al. 2010; Cohen-Kami et al. 2011) by the presence of methylated cytosine. The level of target DNA digestion is interrogated using similar techniques as in case of bisulfite modification. Methylation status comparison between control and test genomic DNA samples can be performed employing differential methylation hybridization (DMH) technique (Huang et al. 1999). Genomic arrays of CpG islands are used to hybridize genomic DNA digested with methylation-sensitive endonucleases and amplified by PCR.

A number of restriction endonucleases sensitive to cytosine methylation are available commercially. Many are used in different techniques to assess methylation status of individual CpG targets or methylation signatures of genomic samples. For example, restriction endonucleases BstUI (CGCG), HpaII (CCGG), and HhaI (GCGC) were used in differential methylation hybridization (DMH) experiments to reveal methylation status differences between control and test samples of genomic DNA (Yan et al. 2002). Another example of methylation status analysis also employs the set of four restriction endonucleases sensitive to cytosine methylation AciI (CCGC), HpaII (CCGG), HinP1I (GCGC), and HpyCH4IV (ACGT) and next generation sequencing approach (Colaneri et al. 2011). In both examples the authors have used only methylation sensitive restriction endonuclease digestion analysis.

It is possible to analyze the methylation level of genomic DNA with restriction enzyme isoschizomer pairs, where the enzymes in the pair have differing sensitivities to CpG methylation. To date there is only one pair of restriction endonucleases, MspI and HpaII, with these capabilities. MspI and HpaII are isoschizomers that recognize the target sequence 5'-CCGG-3'. When the internal CpG in the 5'-CCGG-3' tetranucleotide sequence is methylated cleavage with HpaII is blocked, but cleavage with MspI is not affected. Thus parallel digestions of genomic DNA samples with MspI and HpaII can be used to determine the methylation level of the internal cytosine in the CpG base pair located in the sequence 5'-CCGG-3' (Hatada et al. 2006; Khulan et al. 2006; Oda et al. 2009; Takamiya et al. 2009).

This method is only able to examine methylation status in the context of 5'-CCGG-3' and some genes or gene regions of interest, e.g., AT rich regions, could have no CCGG sites.

Conversely, in CpG rich sequences such as gene promoters where regions of CpG islands are located, there may be many adjacent HpaII/MspI sites, so that methylation analysis of individual CpG base pairs employing HpaII/MspI digestion and qPCR quantification could be impaired as even short qPCR amplicons could have several 5'-CCGG-3' sequences. In particular, after restriction digestion, products are analyzed by qPCR with a primer pair flanking the CCGG site of interest. HpaII/MspI sites may be too close to each other in CpG islands to successfully design amplicon suitable for qPCR analysis; for optimal PCR efficiency a qPCR amplicon usually is about 100 bases length. Moreover, the cleavage of both HpaII and MspI is blocked by m5C modification of the outer cytosine in the 5'-CCGG-3' recognition sequence, and in some cases this could impair the interpretation of CpG methylation status in the target sequence.

Further analysis methods involve enrichment of DNA carrying methylated cytosines from the total pool of shared or fragmented DNA using methylated DNA immunoprecipitation (MeDIP or mDIP) technique (Weber et al. 2005). Enriched methylated DNA fragments can be further analyzed using high-throughput DNA analysis methods such as DNA microarrays (MeDIP-chip) or next generation sequencing (MeDIP-seq). Sequencing is the most informative and preferred analysis technique, whether it is used in combination with bisulfite modification, methylation-sensitive DNA digestion, or DNA immunoprecipitation. Although next generation sequencing (NGS) prices remain high, continuously increasing capabilities and decreasing cost of NGS in the near future should provide an opportunity to perform whole genome or at least exome methylation analysis as a routine approach in diagnostic laboratories.

Despite the above methods, and in view of the awareness of potential importance of DNA methylation in phenotype, the need exists for further tools that can be used to analyze DNA modification status in the rapidly growing field of epigenetic research.

SUMMARY OF THE INVENTION

In one embodiment, the invention provides a restriction endonuclease with a recognition sequence 5'-TCGA-3', which restriction endonuclease is sensitive to the presence of a modified cytosine residue in the recognition sequence.

The inventors found and characterized a restriction endonuclease that can be used to digest DNA comprising the recognition sequence 5'-TCGA-3', and which is sensitive to the presence of a modified cytosine residue in the recognition sequence. In particular, the restriction endonuclease is sensitive to the methylation of the cytosine residue in the recognition sequence, such that when the CpG in the 5'-TCGA-3' is methylated, cleavage with the restriction endonuclease is blocked or significantly reduced. Thus, the restriction endonuclease of the invention is useful in the analysis of DNA methylation.

In one embodiment, the invention provides a method for digesting double-stranded DNA comprising a recognition sequence 5'-TCGA-3' in which the cytosine residue is unmodified. The method comprises a step of contacting the double stranded DNA with the restriction endonuclease.

In one embodiment, the invention provides a method for determining the presence or absence of a cytosine modification in a recognition sequence 5'-TCGA-3' comprised in double stranded DNA. The method comprises (a) contacting the double stranded DNA with the restriction endonuclease to digest the double stranded DNA comprising a recognition sequence in which the cytosine residue is unmodified into reaction products; and (b) determining the presence or absence of reaction products.

The new restriction endonuclease of the invention is an isoschizomer of the known enzymes specific for the target recognition sequence 5'-TCGA-3', such as TaqI, but has a different sensitivity to cytosine modifications, and in particular CpG methylation. As such, the inventive restriction endonuclease also recognizes the same target sequence 5'-TCGA-3', but when the internal CpG in the 5'-TCGA-3' tetranucleotide sequence is methylated cleavage with the inventive restriction endonuclease is blocked or significantly reduced. In contrast cleavage with the other enzymes and especially TaqI is not significantly affected. This presents opportunities for using the inventive restriction endonuclease in methods of DNA methylation analysis, in particular in combination with the non-methylation sensitive isoschizomers.

In one embodiment, the invention provides a method for determining the level of methylation in double stranded DNA. The method comprises (a) contacting a first sample of the double stranded DNA with a methylation sensitive restriction endonuclease as described above to digest the DNA comprising a recognition sequence 5'-TCGA-3' in which the cytosine residue is unmethylated; and (b) determining the amount of undigested DNA and/or determining the amount of digested DNA.

In this embodiment the method may also include the additional steps of (c) contacting a second sample of the double stranded DNA with a second restriction endonuclease; and (d) determining the amount of DNA digestion, where the second restriction endonuclease has a recognition sequence 5'-TCGA-3' and is not sensitive to methylation of the cytosine residue.

In one embodiment, the invention provides a kit for determining the modification status of a DNA duplex substrate. The kit comprises in separate containers (a) a restriction endonuclease as described above; and (b) a second restriction endonuclease that has a recognition sequence 5'-TCGA-3' and is not sensitive to modification of the cytosine residue in the recognition sequence. In one embodiment, the second restriction endonuclease is TaqI, as indicated above.

BRIEF DESCRIPTION OF THE DRAWINGS

FIGS. 5A, 5B, 5C show amplification of 130 bp DNA fragment performed on 5×10$^4$ copies of either non-modified (FIG. 5A) or M.SssI methylated (FIG. 5B) lambda DNA; with residual amounts (%) of undigested DNA target (FIG. 5C).

FIG. 7A, 7B, 7C show spiked PCR fragment digestion analysis in the presence of human Jurkat cell line genomic DNA.

DETAILED DESCRIPTION

Figure 1:
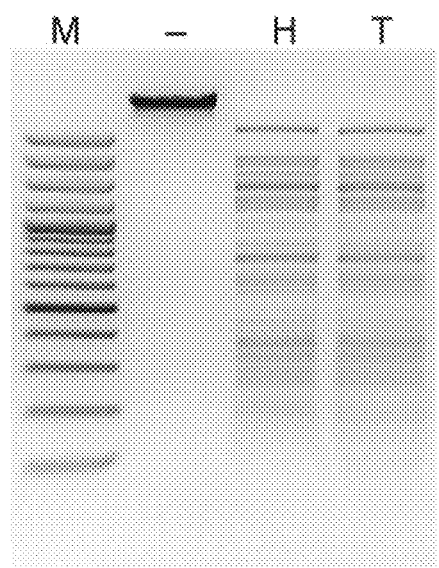
FIG. 1 is a photograph of a gel showing Lambda DNA (dam$^+$, dcm$^+$) digestion with TaqI (5'T↓CGA-3') and HpyF30I.

FIG. 1 is a gel picture showing Lambda DNA (dam+, dcm+) digestion with TaqI (5'T↓CGA-3') and HpyF30I. Lane M: GeneRuler™100 bp Plus DNA Ladder; Lane–: undigested λDNA; Lane H: λ DNA digested with HpyF30I; and Lane T: λ DNA digested with TaqI.

Figure 2A:
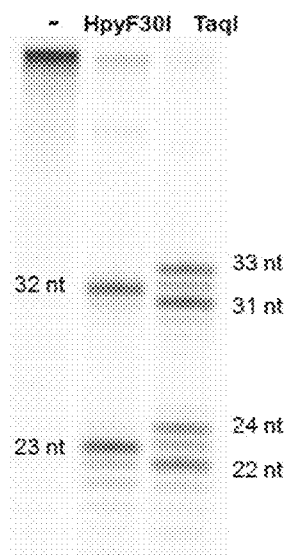
FIGS. 2A, 2B, 2C show the determination of HpyF30I DNA cleavage position.
Figure 2B:
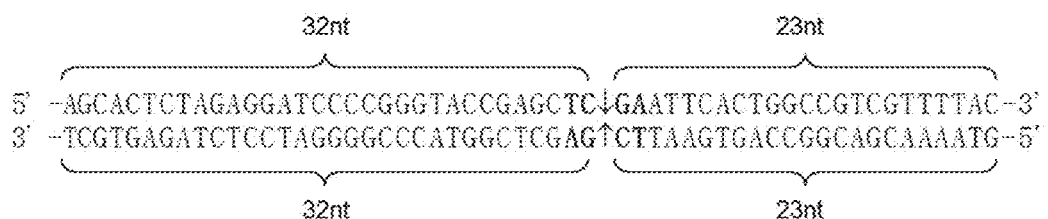
Figure 2C:
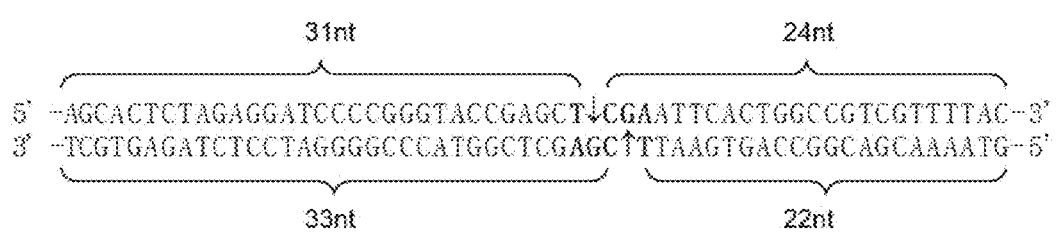

FIGS. 2A to 2C show the determination of HpyF30I DNA cleavage position. 55 nt length double-stranded synthetic oligonucleotide (as shown in FIG. 2B and FIG. 2C, upper strand SEQ ID NO: 9; lower strand SEQ ID NO: 10) containing one TCGA sequence was digested either with HpyF30I or with TaqI, γ-33P-labeled with T4 DNA polynucleotide Kinase, resolved on 15% PAGE/7% urea gel and visualized using phosphorimager Typhoon Trio. FIG. 2A shows the cleavage pattern of digestion of the oligonucleotide with HpyF30I or TaqI (indicated above the gel picture). "–" marks undigested oligonucleotide. Length of single-stranded oligonucleotides generated after cleavage by restriction endonucleases (REs) and separation on denaturing PAGE are indicated. FIGS. 2B and 2C show the sequence of the oligonucleotide digested with HpyF30I or TaqI, respectively. The recognition sequence of REs is shown in bold, cleavage positions are shown by arrows. Length of single-stranded oligonucleotides generated after digestion with REs and separation on denaturing PAGE are indicated.

Figure 3:
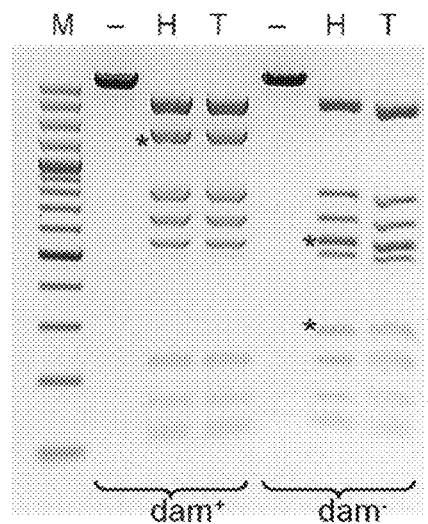
FIG. 3 is a photograph of a gel showing the sensitivity of HpyF30I to Dam methylation.

FIG. 3 is a gel picture showing the sensitivity of HpyF30I to Dam methylation. pSEAD8 (dam+) and pSEAD8 (dam−) were digested with HpyF30I or TaqI and analyzed on 2% agarose gel in TBE buffer. Lane M: GeneRuler™ 100 bp Plus DNA Ladder Lane–: undigested DNA; Lane H: DNA digested with HpyF30I; Lane T: DNA digested with TaqI. Asterisks denote differences in cleavage pattern of dam+ and dam− DNA.

Figure 4:
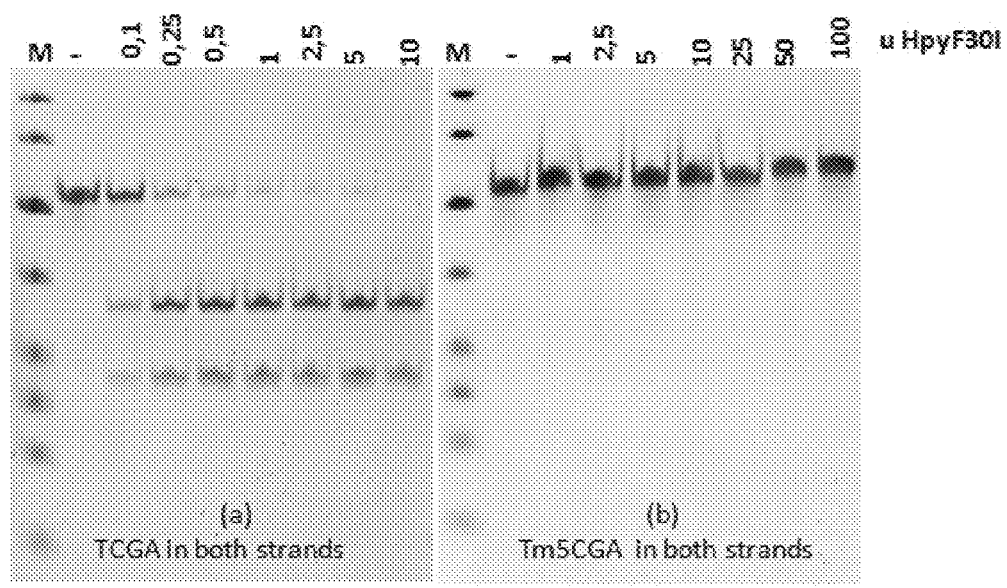
FIG. 4 is a photograph of a gel showing digestion of double-stranded oligonucleotides containing non-modified or m5D modified in both strands HpyF30I recognition sequence TCGA.

FIG. 4 is a gel picture of the digestion of double-stranded oligonucleotides containing non-modified or m5C modified in both strands HpyF30I recognition sequence TCGA. Double-stranded synthetic oligonucleotide (55 bp) with (a) non-modified or (b) m5C modified in both strands HpyF30I recognition site was digested with increasing amounts of HpyF30I (indicated on the top of the gel picture). Reaction products were analyzed on 10% polyacrylamide gel. Undigested oligonucleotide (negative control) is indicated by "–" sign. Lane M—GeneRuler™ Ultra Low Range DNA Ladder.

FIGS. 5A to 5C show the amplification of 130 bp DNA fragment performed on 5×10$^4$ copies of either non-modified (FIG. 5A) or M.SssI methylated (FIG. 5B) lambda DNA (dam−) digested with HpyF30I or TaqI. qPCR reactions were performed on Corbett Rotor-Gene 6000™ (Qiagen) instrument. The amplification plots (FIGS. 5A and 5B) show the difference in amplification of HpyF30I or TaqI digested or undigested TCGA target within lambda DNA. NTC denotes amplification curve from non-template control. The obtained Cq values were used to calculate residual amounts (%) of undigested DNA target (FIG. 5C).

Figure 6:
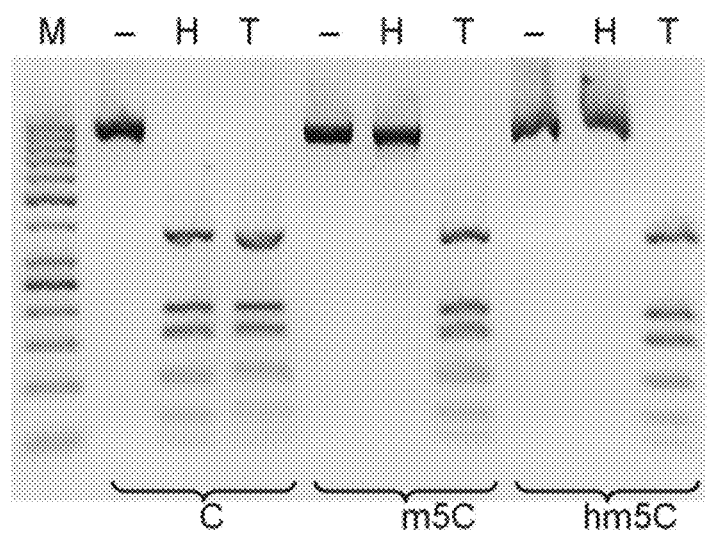
FIG. 6 is a photograph of a gel showing digestion of PCR fragments with m5C or hm5C modifications in both strands of TCGA sequence.

FIG. 6 is a gel picture of the digestion of PCR fragments with m5C or hm5C modifications in both strands of TCGA sequence. 1 μg of double-stranded 962 bp PCR fragment with non-modified, m5C methylated or hm5C (hydroxymethylated) recognition site (indicated below the gel picture) was digested with HpyF30I or TaqI. Reaction products were analyzed on 3% agarose gel in TBE buffer. Lane M: GeneRuler™ 50 bp DNA Ladder; Lane H: DNA digested with HpyF30I; Lane T: DNA digested with TaqI. Undigested DNA (negative control) is indicated by "–" sign.

FIGS. 7A to 7C show spiked PCR fragment digestion analysis in the presence of human Jurkat cell line genomic DNA. Amplification of 130 bp DNA fragment was performed using 5×10$^4$ copies of PCR fragment containing either C (FIG. 7A) or m5C (FIG. 7B) in both strands digested with HpyF30I or TaqI in the presence of human Jurkat cell line genomic DNA. Reactions were performed on StepOnePlus™ (Applied Biosystems) instrument. The amplification plots and melting curves show the difference in amplification of digested or undigested TCGA target within PCR fragment (FIGS. 7A and 7B). NTC denotes amplification curve from non-template control. The obtained Cq values were used to calculate residual amounts (%) of undigested DNA target (FIG. 7C).

Figures 8A, 8B:
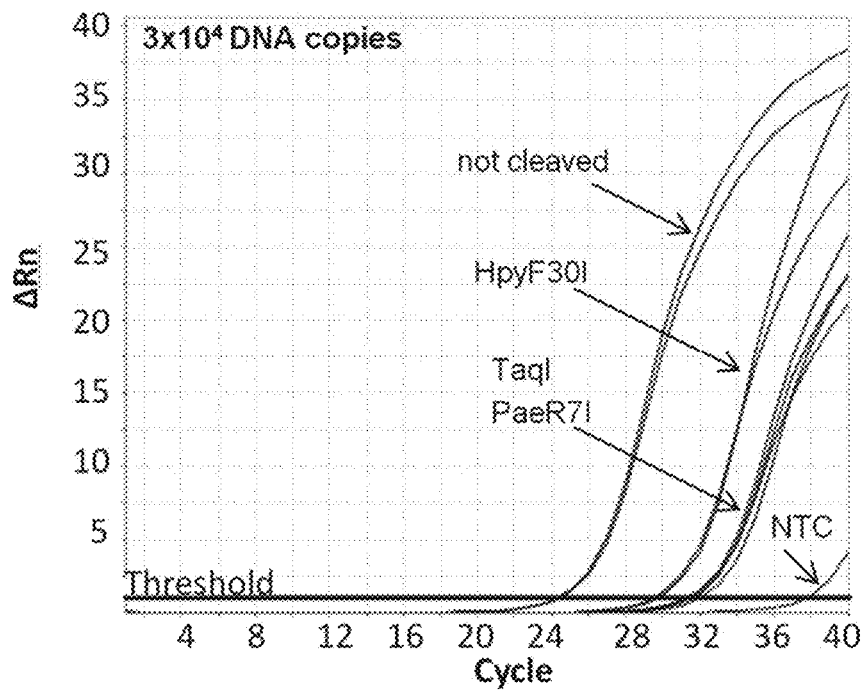
FIGS. 8A, 8B show methylation analysis of DAPK1 gene promoter region in human Jurkat cell line genomic DNA by HpyF30I/TaqI/PaeR7I restriction and subsequent qPCR.

FIGS. 8A and 8B show methylation analysis of DAPK1 gene promoter region in human Jurkat cell line genomic DNA by HpyF30I/TaqI/PaeR7I restriction and subsequent qPCR. Amplification of 106 bp DNA fragment was performed on 3×10$^4$ copies of undigested human Jurkat cell line genomic DNA and genomic DNA digested with HpyF30I, PaeR7I or TaqI. HpyF30I and TaqI restriction endonucleases cleave the same TCGA recognition target within the analyzed qPCR amplicon. PaeR7I restriction endonuclease cleaves CTCGAG target (with TCGA tetranucleotide inside), is sensitive to inner cytosine methylation (REBASE Enzyme No. 1451) and is used as a reference enzyme to test methylation level of DAPK1 gene. Reactions were performed on StepOnePlus™ (Applied Biosystems) instrument. The amplification plots show the difference in amplification of digested or undigested CTCGAG target within DAPK1 gene promoter region (FIG. 8A). NTC denotes amplification curve from non-template control. The obtained Cq values were used to calculate residual amounts (%) of undigested DNA target (FIG. 8B).

Figures 9A, 9B:
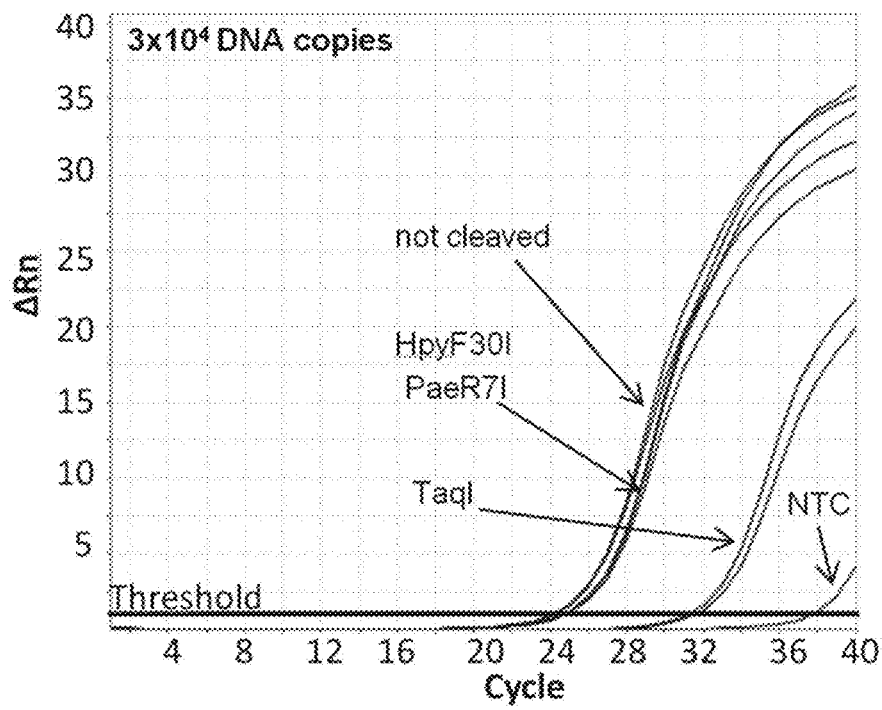
FIGS. 9A, 9B show methylation analysis of RASSFA1 gene promoter region in human Jurkat cell line genomic DNA by HpyF30I/TaqI/PaeR7I restriction and subsequent qPCR.

FIGS. 9A and 9B show methylation analysis of RASSFA1 gene promoter region in human Jurkat cell line genomic DNA by HpyF30I/TaqI/PaeR7I restriction and subsequent qPCR. Amplification of 150 bp DNA fragment was performed on 3×10$^4$ copies of undigested human Jurkat cell line genomic DNA and genomic DNA digested with HpyF30I, PaeR7I or TaqI. HpyF30I and TaqI restriction endonucleases cleave the same TCGA recognition target within the analyzed qPCR amplicon. PaeR7I restriction endonuclease cleaves CTCGAG target (with TCGA tetranucleotide inside), is sensitive to inner cytosine methylation (REBASE) and is used as a reference enzyme to test methylation level of RASSFA1 gene promoter region. Reactions were performed on StepOnePlus™ (Applied Biosystems) instrument. The amplification plots show the difference in amplification of digested or undigested CTCGAG target within RASSFA1 gene promoter region (FIG. 9A). NTC denotes amplification curve from non-template control. The obtained Cq values were used to calculate residual amounts (%) of undigested DNA target (FIG. 9B).

Figure 10:
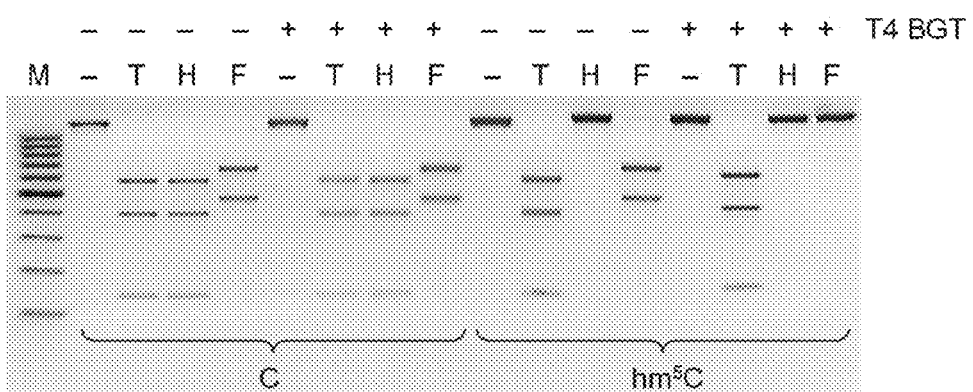
FIG. 10 shows digestion of PCR fragments containing C or hm5C in both DNA strands after treatment with T4 β-glucosyltransferase.

FIG. 10 shows digestion of PCR fragments containing C or hm5C in both DNA strands after treatment with T4 β-glucosyltransferase (T4 BGT). Double-stranded 1095 bp length PCR fragments with non-modified C or hm5C (hydroxymethylated) in both strands (indicated below the gel picture) were treated with T4 BGT (control reactions were incubated without T4 BGT) and subsequently digested with TaqI, HpyF30I or FastDigest™Mfel. Reaction products were analyzed on 2% agarose gel in TBE buffer. M: GeneRuler™ 50 bp DNA Ladder; T: DNA digested with TaqI; H: DNA digested with HpyF30I; F: DNA digested with FastDigest™Mfel. Undigested DNA (negative control) is indicated by "−" sign.

The invention provides a restriction endonuclease (restriction enzyme) with a recognition sequence or target sequence 5'-TCGA-3', which restriction endonuclease is sensitive to the presence of a modified cytosine residue in the recognition sequence.

The modified cytosine residue may be a natural modification, such as N4-methylcytosine, 5-methylcytosine, 5-hydroxymethylcytosine, glucosylated-hydroxymethylcytosine, or 5-carboxylcytosine (5caC), or may be a synthetic modification such as 3-methylcytosine, 5-ethynylcytosine or 5-phenylcytosine. In one embodiment, the modified cytosine residue is not N4-methylcytosine.

In one embodiment, the cytosine is modified at position 5 or the modification comprises a methyl group. In one embodiment, the modified cytosine residue is a methylated cytosine residue and the cytosine is methylated at position 5, i.e. the cytosine is modified with a group that includes a methyl group at position 5. In one embodiment, the methylated cytosine is 5-methylcytosine (m5C), 5-hydroxymethylcytosine (hm5C), or glycosylated 5-hydroxymethylcytosine.

The restriction endonuclease is modification sensitive such that when the cytosine in the recognition sequence is modified the endonuclease has a reduced ability to cleave the sequence, i.e. the endonuclease's cleavage of the recognition sequence 5'-TCGA-3' is blocked or impaired by the cytosine modification. In one embodiment, an impaired ability to cleave the recognition sequence means that under conditions at which the restriction endonuclease is most active, optimal reaction conditions, the presence of the modified cytosine residue in the recognition sequence reduces the endonuclease's ability to cleave the sequence by more than 80% in one embodiment, and more than 90% in one embodiment. In one embodiment when there is a modified cytosine residue in the recognition sequence, e.g., a methylated cytosine residue such as 5mC or hm5C, the endonuclease cleaves ≤5% of the recognition sequences present. The percent of DNA cleavage can be determined by qPCR analysis.

Restriction endonucleases according to the invention can be obtained from *Helicobacter* species, in one embodiment *Helicobacter pylori*. Suitable species and strains are publicly available, and presence of the inventive enzyme in the strain can be determined by testing the enzymatic activity of crude cell extracts.

A restriction endonuclease according to the invention may comprise an amino acid sequence SEQ ID NO: 4, or a sequence having at least 70% identity, at least 80% identity, at least 85% identity, at least 90% identity, or at least 95% identity therewith.

```
                                             SEQ ID NO: 4
MQFLNQSLGFFNKGHFEPIDRNFITESYQALKPIEEIQNKYNKHDNDSFL

NELRDSMVALYLDYELINIQKHGLDAKRSSSDEFLEIKQVSFQSKTWSAT

FNDTTLEKAKVFCDIKTTLAVGVWNNISNLLFIVYGKHPEIGLYLEQKVK

ECHNESRRSTQTIGVSKLIKEFDFKMKPIDLKEQELINLFNLKFGHFSWE

NHLA
```

A restriction endonuclease according to the invention may be encoded by the nucleotide sequence SEQ ID NO: 3 (the nucleotide sequence of the hpyF30IR gene) or a nucleotide sequence having at least 70% identity, at least 80% identity, at least 85% identity, at least 90% identity, or at least 95% identity therewith.

```
                                             SEQ ID NO: 3
atgcaatttttaaatcaatctttgggattttttaataaagggcactttga gcccattgacagaaacttcatcacagaaagctatcaagcactaaagccga ttgaagaaattcaaaataaatacaataaacatgacaacgattcattttg aatgaattgagagatagcatggtggctctatatttagattatgagcttat caatattcaaaagcatggtcttgatgccaaaagaagttcaagcgatgaat ttttagaaatcaaacaagtgtcctttcaaagtaaaacttggagcgcgact tttaatgacaccactttagaaaaagccaaagttttttgcgatattaaaac gactttagccgtgggcgtttggaataatatttctaatcttttattcattg tttatggaaagcaccctgaaattggcttgtatttagaacaaaaagtaaaa gagtgtcataatgagagcaggcgttcaactcaaacgatagggggttagtaa attgatcaaagaatttgattttaaaatgaaacccattgatttaaaagaac aagagcttatcaatcttttttaatcttaaatttggtcattttttcttgggaa aaccatcttgcataa
```

Sequence variants are described below, but in general variations to the amino acid and nucleotide sequence can be made that result in conservative amino acid substitutions. Structurally and functionally significant areas of the enzyme can be identified by mutational and/or structural analysis methods known in the art, or can be predicted from amino acids sequence alignment with sequences of other functionally similar enzymes (Orlowski & Bujnicki, 2008).

In one embodiment the restriction endonuclease is HpyF30I, having the amino acid sequence SEQ ID NO: 4. However, the sequence of other restriction endonucleases according to the invention are provided in Genbank, e.g.,

```
AD005010.1 - hypothetical protein HPSAT_01305 [Helicobacter pylori Sat464]
(SEQ ID No: 11):
  1 mqflnqslgf fnkghfepid rnfitesyqa lkpieeiqnk ynkhdndsfl nelrdsmval 61 yldyeliniq khgldakrss sdefleikqv sfqsktwsat fndttlekak vfcdikttla
```

```
121 vgvwnnisnl lfivygkhpk iglyleqkvk echnesrrst qtigvsklik kfdfkmkpid 181 lkeqelinlf nlkfghfswe nhla
```

AEN17973.1 - hypothetical protein HPPN135_01350 [*Helicobacter pylori* Puno135]
(SEQ ID No: 12):
```
  1 mqflnqslqf fnkghfkpid rnfitesyqa lkpieeiqnk ynkhdndsfl nelrdsmval 61 yldyeliniq khgldakrss sdefleikqv sfqsktwsat fndttlekak vfcdikttla 121 vgvwnnisnl lfivygkhpk iglyleqkak echnesrrst qtigvsklik efdfkmkpid 181 lkeqelinlf nlkfghfswe nhla
```

ACX97473.1 - hypothetical protein KHP_0259 [*Helicobacter pylori* 51]
(and BAJ54865.1 - hypothetical protein HPF16_0268 [*Helicobacter pylori* F16])
(SEQ ID No: 13):
```
  1 mqflnqslgf fnkghfepid rnfiaesyqa lkpieeiqnk ynkhdndsfl nelrdsmval 61 yldyeliniq khgldakrsl sdefleikqv sfqsktwsat fndttlekak vfcdikttla 121 vgvwnnisnl lfivygkhpk iglyleqkvk echnesrrst qtigvsklik efdfkmkpid 181 lkeqelinlf nlkfghfswe nhla
```

ADO03503.1 - hypothetical protein HPCU_01630 [*Helicobacter pylori* Cuz20]
(SEQ ID No: 14):
```
  1 mqflnqslgf fnkghfepid rnfitesyqa lksieeiqnk ynkhdndsfl nelrdsmval 61 yldyeliniq khgldakrns sdefleikqv sfqsktwsat fndttlekak vfcdikttla 121 vgvwnnisnl lfivygkhpk iglyleqkvk echnesrrst qtigvsklik efdfkmkpid 181 lkeqelinlf nlkfghfswe nhla
```

BAJ57132.1 - hypothetical protein HPF30_1035 [*Helicobacter pylori* F30]
(SEQ ID No: 15):
```
  1 mqflnqslgf fnkghfepid rtfitesyqa lkpiekiqnk ynkhdndsfl nelrdsmval 61 yldyeliniq khgldatrss sdefleikqv sfqsktwsat fndttlekak vfcdikttla 121 vgvwnnisnl lfivygkhpk iglyleqkvk echnesrrst qtigvsklik efdfkmkpid 181 lkeqelinlf nlkfghfswe nhla
```

BAJ57852.1 - hypothetical protein HPF32_0270 [*Helicobacter pylori* F32]
(SEQ ID No: 16):
```
  1 mrflnqslgf fnkgcfepid rnfiaesyqa lkpieeiqnk ynkhdndsfl nelrdsmval 61 yldyeliniq khgldakrss sdefleikqv sfqsktwsat fndttlekak vfcdikttla 121 vgvwnnisnl lfivygkhpk iglyleqkvk echnesrrst qtigisklik efdfkmkpid 181 lkeqelinlf nlkfghfswe nhla
```

ACX98882.1 - hypothetical protein HPKB_0272 [*Helicobacter pylori* 52]
(SEQ ID No: 17):
```
  1 mrflnqslgf fnkgrfepid rnfitesyqa lkpieeiqnk ynkhdndsfl nelrdsmval 61 yldyeliniq khgldakrss sdefletkqv sfqsktwsat fndttlekak vfcdvkttla 121 vgvwnnisnl lfivygkhpe ivlyleqkvk echnesrrst qtigvsklik efdfkmkpid 181 lkeqelinlf nlkfghfswe nhla
```

ZP_03438878.1 - hypothetical protein HP9810_1g62 [*Helicobacter pylori* 98-10]
(and EEC23581.1 - hypothetical protein HP9810_1g62 [*Helicobacter pylori* 98-10])
(SEQ ID No: 18):
```
  1 mqflnqslgf fnkghfepid rnfiaesyqa lkpieeiqnk ynkhdndsfl nelrnsival 61 yldyeliniq khgldakrss sdefleikqv sfqsktwsat fndttlekak vfcdikttla 121 vgvwnnisnl lfivygkhpk iglyleqkvk echnesrhst qtigvskltk efdfkmkpid 181 lkeqelinlf nlkfghfswe nhla
```

-continued

ZP_03436984.1 - hypothetical protein HPB128_21g37 [*Helicobacter pylori* B128]
(and YP_003729323.1 - hypothetical protein HPB8_71302 [*Helicobacter pylori* B8],
EEC25275.1 - hypothetical protein HPB128_21g37 [*Helicobacter pylori* B128] and
CBI66859.1 - conserved hypothetical protein [*Helicobacter pylori* B8])(SEQ ID No: 19):

```
  1 mqflnqslgf fnkgcfepid rnfitesyqa lkpieeiqnk ynkhdndsfl nelrdsmval 61 yldyeliniq khgldakrss sdefleikqv sfqsktwsat fndttlekak vfcdikttla 121 vgvwnnisnl lfivygkhpe iglyleqkvk echnesrrst qtigvsklik efdfkmkpid 181 lkeqelinlf nlkfghfs
```

ADU84288.1 - hypothetical protein HPSA_01320 [*Helicobacter pylori* SouthAfrica7]
(SEQ ID No: 20):

```
  1 mqflnqslgf fnkgcfepid rnfitesyqa lkpiekiqnk ynkhdndsfl nelrdsmval 61 yldyelintq khgldakrss sdefleikqv ffqsktwsat fndttlekak vfcdikttla 121 vgvwnnisnl lfivygkhpe mglyleqkvk echnesrrst qtigisklik efdfkmkpid 181 skeqelinlf nlkfgrfswe nyla
```

ADU81143.1 - hypothetical protein HPGAM_01475 [*Helicobacter pylori* Gambia94/24]
(SEQ ID No: 21):

```
  1 mqflngslgf fnkgcfepid rnfitesyqa lkpieeiqnk ynkhdndsfl nelrdsmval 61 yldynlintq khgldakrss sdefleikqv sfqsktwsat fndttlekak vfcdikttla 121 vgvwnnisnl lfivygkhpe mglyleqkvk echnesrrst qtigisklik efefkmkpid 181 skeqelinlf nlkfgrfswe ncla
```

YP_002265873.1 -hypothetical protein HPG27_240 [*Helicobacter pylori* G27]
(AC127007.1 - hypothetical protein HPG27_240 [*Helicobacter pylori* G27] and
GENE ID: 6963126 HPG27_240 - hypothetical protein [*Helicobacter pylori* G27])
(SEQ ID No: 22):

```
  1 mqflnqslgf fnkgcfepid rnfitesyqa lkpieeignk ynkhdndsfl nelrdsmval 61 yldydlintq khgldakrss ndefleikqv sfqsktwsat fndttlekak vfcdikttla 121 vgvwnnisnl lfivygkhpe mglyleqkvk echnerrrst qtigisklik efdskmkpid 181 skeqelinlf nlkfgrfswe nyla
```

YP_665084.1 - hypothetical protein Hac_1347 [*Helicobacter acinonychis* str. Sheeba]
(and CAK00085.1 - hypothetical protein Hac_1347 [*Helicobacter acinonychis* str.
Sheeba)(SEQ ID No: 23):

```
  1 mqflnqsldf fnkgcfepid rnfitescqa lkpiekiqnk ynkhdndsff nelrdsmval 61 fldydlintq khgldakkvq gnefleikqv sfqsktwsat fndttlekak vfcdikttla 121 vgvwnnisnl lfivygkhpe iglyleqkvk echngsrrst qtigisklik efsfkmkpid 181 lkeqelinlf klkfgnfswg nyla
```

EGQ80805.1 - hypothetical protein HMPREF9094_0161 [*Fusobacterium nucleatum* subsp.
*animalis* ATCC 51191](SEQ ID No: 24):

```
  1 mwenreekkm fknqnlplfn kgtykeidrv yvsrvqnamf qvmelqeeyg kydndsflne 61 mkdsmvgmyl gyefvnidkh gfdakrksnk ydewlevkqv sfkseswqat fndttiekae 121 afkdiklnla vgvwnkmmel mfivygknye igeylekmvi kckeeqrrst qtisvqslie 181 nynfrvkpvn nsskeveell kirfkkynwr dridke
```

ZP_06753958.1 - conserved hypothetical protein [*Simonsiella muelleri* ATCC 29453]
(and EFG30885.1 - conserved hypothetical protein [*Simonsiella muelleri* ATCC 29453)
(SEQ ID No: 25):

```
  1 mteqvffknq dlkifhkgny qeinrdfise anhaikplnv iqkkykkldn dtffnelrdg 61 migaylgydl vniekhglda knsennqfle vkqasfsaks wvatfndtty ekaeafedek 121 lflavgvwag lsellfivyg qnpliggylk srvdifksgg svrstqsiti kdlvvcygfk 181 ilfptqerke iknifrlkyk gedwwsgafv de
```

Other embodiments of the restriction endonuclease of the invention are that it is a neoschizomer of Taq I, and in one embodiment cuts in the middle of the recognition/target sequence to form blunt ended fragments, (i.e. 5'-TC↓GA-3'. In addition, or alternatively, the cleavage of the restriction endonuclease is blocked by methylation of adenine (m6A) in the recognition sequence.

In one embodiment a composition comprises the restriction endonuclease described above and a buffer. The buffer is suitable for long term stable storage of the restriction endonuclease. Suitable components for endonuclease storage buffers are known in the art. The storage buffer may comprise potassium phosphate, NaCl, EDTA, DTT, Triton X-100, BSA and/or glycerol.

The invention also provides an isolated polynucleotide encoding the restriction endonuclease of the invention. The polynucleotide may be DNA or RNA. The polynucleotide may comprise SEQ ID NO: 3, or a sequence having at least 70% identity, at least 80%, at least 85%, at least 90% identity, or at least 95% identity therewith.

In one embodiment, the isolated polynucleotide of the invention is in a vector, a carrier vehicle that can be used to transfer the polynucleotide into a host cell. In one embodiment, the polynucleotide in the vector is under the control of an inducible promoter. In one embodiment, the invention provides a host cell that is resistant to cleavage by the restriction endonuclease of the invention, with the vector. The host cell can be used in the production of the restriction endonuclease. A suitable production method comprises culturing the host cell under conditions that allow for the expression of the restriction endonuclease. Suitable vectors, host cells, methods of production, and conditions for expression are known in the art. The vector can be a plasmid, such as pET. Suitable host cells include *E. coli*. In one embodiment, the host cell should express a suitable methyltransferase to protect the host genome against cleavage by the restriction endonuclease. A suitable methyltransferase is M.HpyF30I having SEQ ID No: 8 or encoded by the nucleotide sequence of the hpyF30IM gene having SEQ ID No:7.

```
                                                      SEQ ID NO: 8
MHKVFIMEALECLKRIEKESIQTIYIDPPYNTKSSNFEYEDAHADYEKWI

EEHLILAKSVLKQSGCIFISIDDNKMAEVKIIANEIFGTRNFLGTFITKQ

ATRSNAKHINITHEYVLSYAKNKAFAPGFKILRTLLPIYAKALKDLMRTI

KNVFRQKGQAQAQLVLKEQIKELSKKEHFNFLKNYNLVDEKGEIYFAKDL

STPSHPRSVAIOEINLFLEPLKSRGWSSDEKLKDLYYQNRLIFKNNRPYE

KYYLKESQDNCLSVLDFYSROGTKDLEKLGLKGLEKTPKPVGLIKYLLLC

STPKDSIILDFFAGSGTTAQAVIEANRDYDLNWSFYLCQKEEKIKNNPQA

VSILKNKGYQNTISNIMLLRLEKIIKRSEYEILR

SEQ ID NO: 7
atgcataaagtttttatcatggaagctttggaatgtttgaaaagaataga aaaagaaagcatccaaaccatctatatagacccccttataacactaaga gttctaactttgaatatgaagacgctcatgctgactatgaaaaatggatt gaagaacacttgattttagcaaagtctgtgttaaaacaaagcggttgtat ttttatttctatagatgacaataaaatggctgaagttaaaatcattgcca atgaaattttggaacgcgcaattttttaggcacttttatcactaaacaa gccacaaggtctaacgctaaacacatcaatattacccatgaatatgtttt aagctacgccaaaaataaagcgttcgctcctggttttaaaatcttacgaa cgcttttgcccatttatgctaaagcattaaaagatttaatgcgaacgatt aaaaatgtttttagacaaaaaggacaagctcaagcccaacttgtcctaaa agaacaaatcaaagagttatctaaaaaagaacattttaattttttaaaaa attataatttggtggatgaaaaaggtgaaatttatttcgctaaagattta tctacgccttcacacccacgcagtgtagcgatacaagaaatcaatctttt tttagaacccttaaaaagcagagggtggagcagcgatgaaaagcttaagg atttatattatcaaaacagacttattttaagaacaatcgcccttatgaa aaatattacctaaaagaatcgcaagataattgtttgagcgtgttggattt ttatagccgacaaggcacaaaagatttagaaaaattaggcctaaaggggc tttttaagacgccaaaacctgtaggattgattaaatatttattgttatgc tccaccccctaaagattctattattttagatttttttgcaggcagtgggac aacagcgcaagcggttatagaagctaatagggattatgatttgaattggt cttttatttgtgtcaaaaagaagaaaaaattaaaaataacccgcaagct gttagcattttaaaaaacaaggggtatcaaaacacgatttcaaacatcat gctgttgcgtttagaaaagatcatcaaaagaagtgaatacgaaattttaa gataa
```

The restriction endonuclease of the invention can be used to cleave DNA comprising the recognition sequence. In one embodiment, the invention provides the use of a restriction endonuclease described above to digest double-stranded DNA, where the double-stranded DNA comprises a recognition sequence 5'-TCGA-3' in which the cytosine residue is unmodified. Alternatively in one embodiment the invention is a method for digesting double-stranded DNA comprising a recognition sequence 5'-TCGA-3' in which the cytosine residue is unmodified; the method comprises a step of contacting the double stranded DNA with a restriction endonuclease as described above.

The restriction endonuclease can be used to determine the presence or absence of a cytosine modification as described above in a recognition sequence 5'-TCGA-3' comprised in double stranded DNA. The double stranded DNA is contacted with the restriction endonuclease to digest the double stranded DNA comprising a recognition sequence in which the cytosine residue is unmodified into reaction products, and the presence or absence of reaction products is assessed to determine the presence or absence of the cytosine methylation. The presence of reaction products may be detected, e.g., using gel electrophoresis.

In one embodiment, the restriction endonuclease can be used to determine the level of cytosine modification, e.g., the level of cytosine methylation, in double stranded DNA. A first sample of the double stranded DNA is treated with the restriction endonuclease to digest the DNA comprising a recognition sequence 5'-TCGA-3' in which the cytosine residue is unmodified, and the level of modification is determined based on the amount of digested DNA and/or the amount of undigested DNA. The amount of digested and/or undigested DNA can be determined using methods known in the art, such as qPCR.

The sample of double stranded DNA is not limited, but in one embodiment it is a sample of genomic DNA.

In one embodiment, the restriction endonuclease can be used in combination with restriction endonuclease (a second restriction endonuclease) that is not cytosine modification sensitive, especially one that is not sensitive to the presence of cytosine methylation, e.g. 5-methylcytosine (m5C) or 5-hydroxymethylcytosine (hm5C)) in the recognition sequence. A further digestion with a second sample of the double stranded DNA is performed with the second restriction endonuclease. The second restriction endonuclease is an isoschizomer of the restriction endonuclease of the invention. The second restriction endonuclease can be any enzyme that has the recognition sequence 5'-TCGA-3' but that is not sensitive to cytosine modification, e.g. not CpG methylation sensitive. In one embodiment, the second restriction endonuclease is TaqI or a mutant thereof. The restriction endonuclease Taq I and mutants thereof are known in the art. The amino acid and gene sequence of TaqI restriction endonuclease are publicly available, e.g. amino acid sequence EMBL No.: AAA27505. The second restriction endonuclease can be one with an amino acid sequence that has at least 80%, at least 85%, or at least 90% sequence identity with SEQ ID No: 26.

```
SEQ ID No: 26:
   1 mastqaqkal etferflasl dlesyqqkyr piktveqdlp relnplpdly ehywkaledn 61 psflgfeeff dhwwekrlrp ldefirkyfw gcsyafvrlg learlyrtav siwtqfhfcy 121 rwnascelpl eaapeldaqg idalihtsgs stgiqikket yrseaksenr flrkqrgtal 181 ieipytlqtp eeleekakra rvngetyrlw akvahhldrl engfvifres yvksielflq 241 knaptlsgli rwdrvaqeal tap
```

The second restriction endonuclease may be TfiTok6A1I, TfII, Tsp32I, or TthB8I (REBASE), which share a high sequence homology with TaqI.

After cleavage of the first and second samples with either the restriction endonuclease of the invention or second restriction endonucleases, i.e., the isoschizomer, the residual amount of undigested DNA can be evaluated using, e.g., qPCR analysis. The total amount of target DNA in the first and second samples can be calculated from the undigested DNA sample. The amount of methylated target is calculated from the first sample digested with the enzyme of the invention. The second sample digested with the second restriction endonuclease (e.g. TaqI) is used as a positive control for DNA digestion completeness.

Such a method provides the possibility to identify the methylation level (0%-100%) of cytosine in the CpG base pair located in the middle of a TCGA recognition sequence. For this type of analysis to be accurately performed, two restriction endonucleases recognizing the same sequence and differing in sensitivity to CpG methylation are required. Previously, as mentioned above, there has only been one pair of restriction endonucleases used in combination for methylation status analysis, i.e. MspI and HpaII, which have the recognition site 5'-CCGG-3'. The methods of the invention involving the combination of enzymes described above is an alternative to HpaII and MspI (recognition sequence 5'-CCGG-3') pair of restriction endonucleases and allows the investigation of methylation state of CpG dinucleotides present in the genome in a different sequence context, thus greatly expanding the assortment of available molecular tools for epigenetic analysis. Similar methods to those currently carried out with HpaII and MspI (Hatada et al. 2006; Khulan et al. 2006; Oda et al. 2009; Takamiya et al. 2009) can also be carried out with the combination of the restriction endonuclease of the invention and the CpG methylation insensitive isoschizomers. Thus, alternative genes and gene regions, e.g., AT rich regions that potentially have no CCGG sites, or gene promoters that are typically CpG rich sequences where there may be too many CCGG sites, are available for methylation analysis. The difference between methylation of 5'-CCGG-3' sites and 5'-TCGA-3' sites within the same genes/gene regions can be investigated using the inventive methods in combination with parallel methods involving HpaII and MspI, or simultaneous restriction analysis using HpaII/MspI, and the inventive enzyme pair could be used to increase qPCR assay sensitivity. In this case several restriction targets, CCGG and/or TCGA, located in close proximity may be interrogated in the analyzed amplicon of qPCR. If the DNA region of interest contains CCGG and TCGA sequences in close proximity, it is possible to digest DNA with HpaII/MspI and the enzyme pair of the invention, and subsequently analyze reaction products in qPCR using the same pair of primers flanking these targets, and to determine CpG methylation level of CpGs located close to each other.

In one embodiment, the invention provides a kit for determining the modification status of a DNA duplex substrate. The kit comprises in separate containers (a) a restriction endonuclease according to the invention; and (b) a second restriction endonuclease. The restriction endonuclease and the second restriction endonuclease of the kit are as described above. In one embodiment, the restriction endonuclease of the invention is sensitive to methylation of the cytosine residue in the recognition sequence 5'-TCGA-3', while the second restriction endonuclease is an isoschizomer and is not sensitive to methylation of the cytosine residue. In one embodiment, the second restriction endonuclease is TaqI.

In one embodiment, the kit further comprises a container of genomic DNA. This can be used for a control reaction involving the enzymes in the kit.

In one embodiment, the kit further comprises one or more containers of reaction buffer for the restriction endonuclease of the invention and/or the second restriction endonuclease. Suitable reaction buffers are known in the art and may comprise Tris-HCl, Tris-acetate, $MgCl_2$, Mg-acetate, K-acetate, NaCl, and/or BSA.

The invention will now be described in further detail, by way of example only, with reference to the following Examples and related Figures.

Example 1

Restriction Endonuclease HpyF30I

Cloning of Restriction Endonuclease HpyF30I from *Helicobacter pylori* RFL30 Strain The gene of HpyF30I restriction endonuclease (REBASE Enz Num 4343) was PCR amplified from *H. pylori* strain RFL30 genomic DNA template using pair of primers, Tq-hpR-dir (GCTATTTAAATGCAATTTTTAAAT-CAATCTTTGGGAT (SEQ ID No: 1)) and Tq-hpR-rev (ATAGCGGCCGCTTATGCAAGATGGTTTTCCCAAG (SEQ ID No: 2)), designed according to the sequence information of *Helicobacter pylori* strain 26695, i.e. the primers were complementary to the 5' and 3' ends of HP0261 ORF. The HP0261 ORF is adjacent to the gene HP0260. Gene HP0260 (hpyF30IM) has previously been found to encode a TCGA-specific methyltransferase M.HpyAORF260 (Vitkute et al. 2001). A pair of primers designed to be complementary to the 5' and 3' ends of gene encoding DNA methyltransferase M.HpyAORF260 from *Helicobacter pylori* 26695 strain, and which were used to amplify the hpyF30IM gene from *H. pylori* RFL30 strain are Tq-hpM-dir1 (CTGCAGAAGGAGATTTAAATG-CATAAAGTTTTTATCATGGAAG (SEQ ID No: 5)) and Tq-hpM-rev (ATAGCGGCCGCTTATCTTAAAATTTCGT-ATTCACTTCT (SEQ ID No: 6)). The nucleotide sequence of hpyF30IM (SEQ ID No: 7) and amino acid sequence (SEQ ID No: 8) of M.HpyF30I are provided above. The amino acid sequence of M.HpyF30I is almost identical to M.HpyAORF260, i.e., has 96% of identical amino acids, which is proved to recognize the same sequence as M. TaqI methyltransferase. According to the sequence analysis methyltransferase M.HpyF30I is proposed to be m6A methyltransferase (Vitkute et al. 2001).

The restriction endonuclease gene was cloned into pET type expression vector and was expressed in *E. coli* ER2566 strain in the background of methyltransferase M.HpyF30I (pACYC184). Nucleotide sequence of hpyF30IR (SEQ ID No: 3) and amino acid sequence of HpyF30I restriction endonuclease (SEQ ID No: 4) are provided above.

Restriction endonuclease HpyF30I was purified to about 90% purity according to SDS-PAGE using several subsequent ion-exchange and affinity chromatography steps. Absence of endo and exonucleases was confirmed using standard labeled oligonucleotide (LO) quality test (http://www.fermentas.com/en/support/technical-reference/restriction-enzymes/quality).

Identification of Other TCGA Specific Methylation Sensitive Enzymes

BLAST search has identified many highly homologous proteins (up to 99% of identical amino acids) in different strains of *Helicobacter pylori*, which are identified as hypothetical proteins in Genbank.

The Specificity of HpyF30I Restriction Endonuclease

*E. coli* genomic DNA in vivo methylated with M.HpyF30I (putative specificity TCGA) was protected against the cleavage of HpyF30I restriction endonuclease. The lambda DNA cleavage pattern with TaqI (5'-T↓CGA-3' prototype restriction endonuclease) and HpyF30I restriction endonucleases are identical (FIG. 1). These data indirectly confirm that HpyF30I restriction endonuclease recognizes the same 5'-TCGA-3' sequence as the prototype restriction endonuclease TaqI. Recognition sequence of HpyF30I restriction endonuclease was directly confirmed in double-stranded synthetic oligonucleotide digestion experiments used to identify the cleavage position of HpyF30I restriction endonuclease (FIGS. 2A to 2C). Even though HpyF30I restriction endonuclease recognition sequence is the same as TaqI, the cleavage position is different. Prototype restriction endonuclease TaqI cleaves TCGA sequence after the T base and produces two nucleotide long cohesive ends (FIG. 2C). Restriction endonuclease HpyF30I cleaves TCGA sequence after the C base (in the middle of recognition sequence) and produces the DNA with blunt ends (FIG. 2B).

Methods and Materials

Lambda DNA digestion. 1 µg of λ DNA (dam$^+$, dcm$^+$) was digested in parallel with 10 units of HpyF30I REase in 30 µl reaction buffer Tango™ (33 mM Tris-acetate; 10 mM Mg acetate; 66 mM K-acetate; 0.1 mg/ml BSA; pH 7.9 at 37° C.) at 37° C. for one h and with TaqI REase in reaction buffer TaqI (10 mM Tris-HCl; 5 mM MgCl$_2$; 100 mM NaCl; 0.1 mg/ml BSA; pH 8.0 at 37° C.) at 65° C. for one h. The reactions were stopped by adding 6×DNA Loading Dye & SDS Solution and resolved on 1.7% agarose gel in TBE buffer.

Identification of DNA cleavage position by HpyF30I restriction endonuclease. To determine DNA cleavage position of HpyF30I, 1 µg 55 nt length double-stranded synthetic oligonucleotide (obtained after annealing of two complementary single-stranded oligonucleotides) containing one TCGA sequence was digested in parallel with 10 units of HpyF30I REase in 25 µl reaction buffer Tango™ at 37° C. for 1 h and with TaqI REase in TaqI reaction buffer at 65° C. for 1 h. Ten µl of reaction products were γ-$^{33}$P-labeled with T4 DNA polynucleotide kinase (using protocol recommended by manufacturer) in 20 µl total volume of reaction mixture containing 50 mM imidazole-HCl (pH 6.4 at 25° C.), 18 mM MgCl$_2$, 50 mM DTT, 0.1 mM spermidine, 0.1 mM ADP, 10 pmol γ-ATP, 10 pmol PEG 6000, and 1 u of the enzyme. Reactions were performed at 37° C. for 30 min and stopped by heating at 75° C. for 10 min. Undigested oligonucleotide was γ-$^{33}$P-labeled using the same reaction conditions and used as negative control. After addition of 2×RNA Loading Dye samples were heated at 95° C. for five min. Ten µl of each were separated on 15% PAGE/7% urea gel in TBE buffer and visualized using phosphorimager Typhoon Trio.

Example 2

Methylation Sensitivity of HpyF30I Restriction Endonuclease

The M.HpyF30I is putative m6A methyltransferase of TCGA specificity. Because *E. coli* DNA in vivo methylated with M.HpyF30I is completely protected against cleavage of HpyF30I, it was deduced that restriction endonuclease is sensitive to m6A modification in TCGA recognition sequence. Restriction endonuclease HpyF30I sensitivity to m6A modification was directly confirmed in DNA digestion experiment with overlapping Dam methylation (FIG. 3). Dam methylation target GATC may overlap the HpyF30I recognition target TCGA in the context of TCGATC sequence. pSEAD8 plasmid DNA, which contains 11 TCGA sequences, one of them overlapping with dam sequence in one strand and the other one in both DNA strands was purified from *E. coli* dam$^+$ strain JM109 and digested with TaqI restriction endonuclease (sensitive to m6A modification) and HpyF30I. DNA cleavage pattern was identical for both enzymes and differed from cleavage pattern of pSEAD8 isolated from dam$^-$ *E. coli* strain GM2163 (FIG. 3). The result indicated that HpyF30I restriction endonuclease likewise TaqI did not cleave hemimethylated and fully methylated TCGm6A targets.

Sensitivity of HpyF30I restriction endonuclease to m5C and hm5C was tested in double-stranded synthetic oligonucleotide digestion, M.SssI methylated lambda DNA digestion and PCR fragment DNA (synthesized with dCTP or dm5CTP, or dhm5CTP) digestion experiments. Double-stranded synthetic oligonucleotide having TCGA recognition site with unmodified C was digested with HpyF30I restriction endonuclease while the oligonucleotide having TCGA sequence with m5C in both strands was completely resistant to HpyF30I treatment even with the highest enzyme amounts used in the experiment (FIG. 4).

Lambda DNA (dam⁻) and lambda DNA (dam⁻) methylated with M.SssI methyltransferase were used to interrogate HpyF30I ability to cleave completely modified TCGA target (m5C present in both DNA strands). Cleavage completeness was evaluated using qPCR performed on dedicated TCGA target within amplification region (FIGS. 5A to 5C). Methylated lambda DNA was completely resistant to HpyF30I cleavage (100% of residual DNA target amplification after restriction reaction), meanwhile only minor amount of undigested target was detected (0.2%) after the treatment with TaqI restriction endonuclease. In the same experiment unmodified lambda DNA target was efficiently digested with both HpyF30I (0.6% of residual DNA target left) and TaqI (0.06%) enzymes.

PCR fragments synthesized using dCTP, dm5CTP or dhm5CTP were used to check HpyF30I sensitivity to C base modifications inside the TCGA recognition sequence (FIG. 6). Ordinary PCR fragment (synthesized with dCTP) was completely digested with HpyF30I restriction endonuclease. Other two PCR fragments (synthesized with dm5CTP or dhm5CTP) could be digested only with TaqI restriction endonuclease, which is not sensitive to C base modification within TCGA sequence, but not with HpyF30I. Experimental data indicated that HpyF30I restriction endonuclease did not cleave TCGA target with m5C and hm5C modification in both strands (FIGS. 4 and 6).

Methods and Materials

Digestion of dam⁺ or dam⁻ DNA by HpyF30I restriction endonuclease. One µg pSEAd8 DNA isolated from *E. coli* dam⁺ or dam⁻ strain and linearized by Eam11051 REaze was digested in parallel with 10 units of HpyF30I REase in 30 µl reaction buffer Tango™ (33 mM Tris-acetate; 10 mM Mg acetate; 66 mM K-acetate; 0.1 mg/ml BSA; pH 7.9 at 37° C.) at 37° C. for one h and with TaqI REase in reaction buffer TaqI (10 mM Tris-HCl; 5 mM $MgCl_2$; 100 mM NaCl; 0.1 mg/ml BSA; pH 8.0 at 37° C.) at 65° C. for one h. The reactions were stopped by adding 6×DNA Loading Dye & SDS Solution and resolved on 2% agarose gel in TBE buffer. 1351 bp DNA fragment obtained after digestion with both REases of dam⁺ DNA (marked by asterisk) contains one TCGA sequence overlapping with dam sequence GATC in one strand and one TCGA sequence overlapping with dam sequence in both strands. Both HpyF30I and TaqI cleaved these sites in dam⁻ DNA generating 289, 502 and 561 bp fragments (marked by asterisks).

Digestion of double stranded DNA oligonucleotides without and with m5C modification within TCGA site by HpyF30I restriction endonuclease. 55 nt length single stranded oligonucleotide (see FIG. 2B upper strand) was annealed with 17 nt length oligonucleotide M13/pUC Forward (experiment (a)). In experiment (b) the 55 nt single stranded oligonucleotide had m5C modification within the TCGA sequence. The 5'-overhang was filled in by T4 DNA polymerase. Reactions were performed in 67 µl buffer Tango™ containing 0.33 nmol of annealed oligonucleotides, dATP, dTTP and dGTP (0.5 mM of each), 17 u of T4 DNA polymerase and (a) 0.5 mM dCTP or (b) 0.5 mM dm5CTP at 11° C. for 30 min and stopped by heating at 75° C. for 10 min. Equal amounts of obtained double-stranded oligonucleotides (1 µg in each reaction) were digested with increasing amounts of HpyF30I in 20 µl of buffer Tango™ at 37° C. for one h. Reactions were stopped by adding 6×DNA Loading Dye & SDS Solution and 10 µl of each were analyzed on 10% polyacrylamide gel in TBE buffer.

Digestion of in vitro methylated (M.SssI methyltransferase) lambda DNA (dam⁻) by HpyF30I restriction endonuclease. Lambda DNA (dam⁻) was modified in vitro by M.SssI DNA methyltransferase according to manufacturer's recommendations (www.fermentas.com/templates/files/tiny_mce/coa_pdf/coa_em0821.pdf). After modification reaction DNA was extracted with chloroform and precipitated with isopropanol (in the presence of 0.3 M NaCl). One µg of obtained m5CpG modified lambda DNA as well as 1 µg of not modified lambda DNA (dam⁻) were digested in parallel with 10 u of HpyF30I REase in 20 µl reaction buffer SdaI (37 mM Tris-acetate; 15 mM Mg acetate; 150 mM K-acetate; 0.1 mg/ml BSA; pH 7.0 at 37° C.) at 37° C. for one h and with TaqI REase in reaction buffer TaqI at 65° C. for one h. After restriction reaction mixtures were serially diluted in $H_2O$ and qPCR reactions were performed on $5 \times 10^5$ to 50 copies of not digested (control reaction) or digested DNA in 25 µl reaction volume of Maxima SYBR Green qPCR master Mix on Corbett Rotor-Gene 6000™ (Qiagen) instrument. 130 bp DNA fragment containing one TCGA site was amplified using primers Lambda_fw (CTGATTCGTGGAACAGATACTC (SEQ ID NO: 27)) and Lambda_rw (ACACTTCAGGAGTGGAACGCA (SEQ ID NO: 28)).

Digestion of PCR fragments synthesized using dCTP, dm5CTP or dhm5CTP by HpyF30I restriction endonuclease. Three 962 bp double-stranded DNA fragments with 6 TCGA sequences were synthesized from plasmid DNA template in PCR reaction mixtures containing buffer for Pfu DNA polymerase, recommended amount of Pfu DNA Polymerase, dATP, dTTP and dGTP, 0.2 mM each and (a) 0.2 mM dCTP, (b) 0.2 mM dm5CTP or (c) 0.2 mM dhm5CTP. PCR products were purified using GeneJET™ PCR Purification Kit. One µg of each PCR fragments were digested in parallel with 5 units of HpyF30I REase in 30 µl of reaction buffer Tango™ at 37° C. for one h and with 5 units of TaqI REase in reaction buffer TaqI at 65° C. for one h. The reactions were stopped by adding 6×DNA Loading Dye & SDS Solution and resolved on 3% agarose gel in TBE buffer.

Example 3

The Interrogation of DNA Methylation Level within TCGA Target in Human Jurkat Cell Line Genomic DNA Using HpyF30I and TaqI Restriction Endonucleases Spiked PCR Fragment Digestion Analysis in the Presence of Human Jurkat Cell Line Genomic DNA Suitability of HpyF30I and TaqI restriction endonucleases for methylation analysis of genomic DNA was first evaluated using either methylated or unmethylated DNA as a spike control together with constant amount (0.5 µg) of human Jurkat cell line genomic DNA. The PCR fragment which was amplified from lambda DNA in presence of either 100% of dCTP or dm5CTP in reaction mixtures subsequently was used as qPCR amplicon to evaluate digestion efficiency by HpyF30I and TaqI restriction endonucleases in the presence of genomic DNA (FIGS. 7A to 7C). Methylated DNA was completely resistant to HpyF30I cleavage (100% of residual DNA target amplification after restriction reaction) meanwhile only minor amounts of undigested target were detected (0.7%) after treatment with TaqI restriction endonuclease. In the same experiment unmodified DNA target was efficiently digested with both HpyF30I (7% of residual DNA target left) and TaqI (0.7%) enzymes. The data indicated that analysis of methylated DNA could be successfully performed in the presence of genomic DNA maintaining the reaction conditions close to the experiment where only genomic DNA would be digested and analyzed.

Methylation Analysis of DAPK1 Gene in Human Jurkat Cell Line Genomic DNA Using HpyF30I/TaqI/PaeR7I Restriction and Subsequent qPCR The methylation analysis of DAPK1 gene promoter region in human Jurkat cell line genomic DNA was performed using the same basic scheme as in all previous experiments. CTCGAG target present in DAPK1 gene promoter region was addressed for restriction analysis with HpyF30I and TaqI enzymes (recognize inner tetranucleotide TCGA) and PaeR7I enzyme (recognize CTCGAG). PaeR7I enzyme is sensitive to methylation of inner cytosine of CTCGAG sequence (REBASE). In this case HpyF30I, TaqI, and PaeR7I cleaving sites overlap and digestion completeness could be compared in cases of PaeR7I and HpyF30I enzymes. The same digestion level for both enzymes was expected if HpyF30I was also sensitive to inner cytosine methylation within CTCGAG target present in DAPK1 gene promoter region. All the restriction endonucleases HpyF30I, PaeR7I and TaqI almost completely cleaved their target leaving 2%, 0.8% and 0.7% of undigested DNA, respectively (FIGS. 8A and 8B). The data indicated that inner cytosine in CTCGAG target present in DAPK1 gene promoter region was completely unmethylated.

Methylation Analysis of RASSFA1 Gene in Human Jurkat Cell Line Genomic DNA Using HpyF30I/TaqI/PaeR7I Restriction and Subsequent qPCR The methylation analysis of RASSFA1 gene promoter region in human Jurkat cell line genomic DNA was performed using the same scheme as in previous experiments with DAPK1 gene analysis. CTCGAG target present in RASSFA1 gene promoter region was addressed for restriction analysis with HpyF30I and TaqI enzymes (recognize inner tetranucleotide TCGA) and PaeR7I enzyme (recognize CTCGAG). PaeR7I enzyme is sensitive to methylation of inner cytosine of CTCGAG sequence (REBASE). In this case HpyF30I, TaqI, and PaeR7I cleaving sites overlap and digestion completeness was compared for PaeR7I and HpyF30I enzymes. The same digestion level for both enzymes was expected if HpaF30I was also sensitive to inner cytosine methylation within CTCGAG target present in RASSFA1 gene. Both restriction endonucleases HpyF30I and PaeR7I performed partial DNA cleavage leaving 50% of undigested target. At the same time TaqI restriction endonuclease, which is not sensitive to cytosine modifications, completely digested tested DNA sample leaving only about 0.8% of undigested DNA (FIGS. 9A and 9B). The data indicated that the level of inner cytosine methylation in CTCGAG target present in RASSFA1 gene promoter region is about 50% as confirmed by digestion with HpyF30I and PaeR7I restriction endonucleases.

Methods and Materials

Digestion of PCR fragments (synthesized using dCTP or dm5CTP) in the presence of genomic DNA. 130 bp DNA fragments containing one TCGA sequence were synthesized from lambda DNA template in PCR with Pfu DNA polymerase using primers Lambda_fw (CTGATTCGTG-GAACAGATACTC (SEQ ID NO: 27)) and Lambda_rw (ACACTTCAGGAGTGGAACGCA (SEQ ID NO: 28)). The reaction mixtures contained buffer for Pfu DNA polymerase, recommended amount of the enzyme, dATP, dTTP and dGTP, 0.2 mM each and 0.2 mM dCTP or 0.2 mM dm5CTP. PCR products were purified using GeneJET™ PCR Purification Kit. 0.5 µg of methylated or unmethylated PCR fragment were mixed with 0.5 µg of human Jurkat cell line genomic DNA (purified with GeneJET™ Genomic DNA Purification Kit) and digested in parallel with 10 units of HpyF30I REase in 30 µl of reaction buffer SdaI at 37° C. for one h and with 10 units of TaqI REase in reaction buffer TaqI at 65° C. for one h. After restriction reaction mixtures were serially diluted in H$_2$O and qPCR reactions were performed on 5×10$^5$ to 50 copies of not digested (control reaction) or digested PCR fragment in 25 µl reaction volume of Maxima SYBR Green qPCR master Mix on StepOnePlus™ (Applied Biosystems) instrument. Primers Lambda_fw and Lambda_rw were used in qPCR.

Methylation analysis of DAPK1 gene in Human Jurkat cell line genomic DNA using HpyF30I/TaqI/PaeR7I restriction endonucleases. One µg of Human Jurkat cell line genomic DNA (purified using GeneJET™ Genomic DNA Purification Kit) was digested in parallel with 10 units of HpyF30I REase in 20 µl reaction buffer SdaI at 37° C. for one h, with 20 units of PaeR7I REase in 20 µl of reaction buffer "4" at 37° C. for one h and with 10 units of TaqI REase in 20 µl of reaction buffer TaqI at 65° C. for one h. The reaction mixtures were then serially diluted in H$_2$O and qPCR reactions were performed on 3×10$^5$ to 30 copies of not digested (control reaction) or digested DNA in 25 µl reaction volume of Maxima SYBR Green qPCR master Mix on StepOnePlus™ (Applied Biosystems) instrument. 106 bp DNA fragment from DAPK1 gene promoter region containing one CTCGAG sequence was amplified using primers DAPK_Tq_fw1 (CTTTTGCTTTCCCAGCCAGG (SEQ ID NO: 29)) and DAPK_Tq_rw1 (GATCGCACTTCTC-CCCGAAG (SEQ ID NO: 30)).

Methylation analysis of RASSFA1 gene in Human Jurkat cell line genomic DNA using HpyF30I/TaqI/PaeR7I restriction endonucleases. In this experiment not digested or HpyF30I/TaqI/PaeR7I digested human Jurkat cell line genomic DNA was amplified using primers complementary to of RASSFA1 gene promoter region: Rasf_fw2 (AAGAT-CACGGTCCAGCCTCT (SEQ ID NO: 31)) and Rasf_rev2 (GCAACACACTTGGCCTACC (SEQ ID NO: 32)). 150 bp qPCR amplicon contains one CTCGAG sequence.

Example 4

The Interrogation of DNA Methylation Level within TCGA Target in RASSFA1 Gene of Human Jurkat Cell Line Genomic DNA Using Bisulphite Treatment To additionally validate that HpyF30I restriction endonuclease can be used for DNA methylation status determination within TCGA target, a bisulfite treatment assay was used. During bisulfite treatment cytosines are converted to uracyl if they are non methylated, while methylated cytosines remain unchanged. Genomic DNA from human Jurkat cell line was treated with sodium bisulfite. Target DNA fragment, namely the RASSFA1 gene promoter region containing TCGA sequence, was then amplified using Taq DNA polymerase and primers specific for converted DNA. The obtained 164 bp length PCR product was cloned into pTZ57R/T cloning vector and 44 individual clones were sequenced and analyzed. Sequence data showed that 20 clones (about 45%) contained cytosines in TCGA sequence indicating that these targets are methylated and thus resistant to bisulfite conversion. In the remaining 24 clones (about 55%) cytosines in TCGA sequence were converted to uracils and were read as thymines in the sequencing reads indicating that they were unmodified in the original genomic DNA.

The bisulfite sequencing experiment results correlated well with the data obtained in the previous experiment, where human Jurkat cell line genomic DNA was cleaved with HpyF3OI restriction endonuclease and digestion level of the same TCGA target in RASSFA1 gene promoter region was analyzed in subsequent qPCR. HpyF3OI digestion resulted in about 50% of not cleaved target, thus indicating about 50% methylation level within the target (FIGS. 9A and 9B). These observations confirmed that HpyF3OI digestion could be used to determine the methylation status of TCGA sequences in eukaryotic genomic DNA.

Methods and Materials

The Conversion Reagent was prepared as follows: 0.9 ml sterile distilled water was mixed with 200 µl 3M NaOH solution and 60 µl dimethylformamide (DMF). Sodium metabisulfite (0.72 g) was added to the solution and dissolved by inverting and shaking for about three min. Prepared Conversion Reagent (120 µl) was added to 475 ng/5 µl DNA solution. The reaction mixture was heated at 98° C. for ten min and subsequently incubated at 60° C. for three h. The bisulfite-treated DNA was purified using EZ Bisulphite DNA Clean-up Kit™ (ZymoResearch).

Purified DNA (3 µl) was used as a template in the amplification reaction with Taq DNA Polymerase (#EP0401) using primers konv_dir (AAATACAC-CCCTAAACCTCAAAATC (SEQ ID NO: 33)) and konv_rev (ATATTTGGTTTATTTATTGGGTGGG (SEQ ID NO: 34)) in 50 µl reaction mixture also containing 0.2 mM dNTP Mix and PCR buffer (#838). The sample was incubated at 95° C. for five min, and then 30 cycles of PCR at 94° C. for 30 s, 55° C. for 30 s and 72° C. for 30 s were performed. The obtained 164 bp length PCR product was purified using GeneJET™ PCR Purification Kit and cloned into pTZ57R/T cloning vector using InsTAclone™ PCR Cloning Kit. Plasmid DNAs were purified from 44 individual colonies and cloned fragments Were sequenced using M13/pUC reverse sequencing primer (GAGCGGA-TAACAATTTCACACAGG (SEQ ID NO: 35)).

Example 5

HpyF3OI Restriction Endonuclease is Sensitive to Glucosylated hm5C

To demonstrate the sensitivity of the enzyme to glucosylated hm5C, PCR fragments containing two TCGA sequences were synthesized using dCTP or dhm5CTP. Half were treated with T4 β-glucosyltransferase (T4-BGT) which adds a glucose moiety to 5-hydroxymethylcytosine. The DNA substrates were then incubated with restriction enzymes. The PCR fragment containing C was digested with HpyF3OI restriction endonuclease while the fragment containing hm5C or glucosylated hm5C was completely resistant to HpyF3OI treatment (FIG. 10). All DNA samples were cleaved by TaqI restriction endonuclease which is not sensitive to C base modifications within the TCGA sequence. The glucosylation reaction was verified by digestion of DNA with FastDigest MfeI (the PCR fragment has one target for this REase) which is not sensitive to hm5C modification in CAATTG sequence but does not cleave DNA when hm5C is glucosylated (FIG. 10).

Methods and Materials

Digestion of PCR fragments (synthesized using dCTP or dhm5CTP) after treatment with T4 BGT. 1095 bp DNA fragments containing two TCGA sequences and one CAATTG sequence (FastDigest™MfeI target) were synthesized from φX174 DNA template in PCR with DreamTaq DNA polymerase using primers X174_for (CACGCCA-GAATACGAAAGACCAG (SEQ ID NO: 36)) and X174_rev (CGATAAACCAACCATCAGCATGAG (SEQ ID NO: 37)). The reaction mixtures contained buffer for DreamTaq DNA polymerase, recommended amount of the enzyme, dATP, dTTP and dGTP, 0.2 mM each and 0.2 mM dCTP or 0.2 mM dhm5CTP. The PCR products were purified using GeneJET™ PCR Purification Kit. 2.5 µg of each PCR fragment were incubated in 150 µl of Epi Buffer with UDP-Glucose and T4 BGT according to manufacturer's recommendations (http://www.fermentas.com/en/products/all/epigenetics/kl481-epijet-5-hmc-analysis-kit). Control reactions were incubated without T4 BGT. After heat inactivation of T4 BGT at 65° C. for ten min, the reaction mixtures were divided into four equal parts and separate samples were incubated with 20 units of TaqI REase at 65° C. for one h, 10 units of HpyF3OI REase or 3 µl of FastDigest™MfeI at 37° C. for one h. Control reactions were incubated without enzymes. The restriction digestion products were then analyzed on 2% agarose gel in TBE buffer.

The following references are expressly incorporated herein by reference in their entirety:

Bemstein et al. (2007) The mammalian epigenome. Cell, 128, 669-681.

Bird (2002) DNA methylation patterns and epigenetic memory. Genes Dev, 16, 6-21.

Bird (2007) Perceptions of epigenetics. Nature, 447, 396-398.

Cohen-Kami et al. (2011). The MspJI family of modification-dependent restriction endonucleases for epigenetic studies. Proc. Natl. Acad. Sci. USA. 108(27): 11040-5

Colaneri et al. (2011) Expanded methyl-sensitive cut counting reveals hypomethylation as an epigenetic state that highlights functional sequences of the genome. Proc Natl Acad Sci USA, 108, 9715-9720.

Esteller (2008) Epigenetics in cancer. N Engl J Med, 358, 1148-1159.

Groth et al. (2007) Chromatin challenges during DNA replication and repair. Cell, 128, 721-733.

Hatada et al. (2006) Genome-wide profiling of promoter methylation in human. Oncogene, 25, 3059-3064.

Holliday and Pugh (1975) DNA modification mechanisms and gene activity during development. Science, 187, 226-232.

Huang et al. (1999) Methylation profiling of CpG islands in human breast cancer cells. Hum Mol Genet, 8, 459-470.

Khulan et al. (2006) Comparative isoschizomer profiling of cytosine methylation: the HELP assay. Genome Res, 16, 1046-1055.

Koch et al. (2007) The landscape of histone modifications across 1% of the human genome in five human cell lines. Genome Res, 17, 691-707.

Kriaucionis and Heintz (2009). The nuclear DNA base 5-hydroxymethylcytosine is present in Purkinje neurons and the brain. Science, 324, 929-930.

Krivtsov et al. (2008) H3K79 methylation profiles define murine and human MLL-AF4 leukemias. Cancer Cell, 14, 355-368.

Mattick and Makunin (2006) Non-coding RNA. Hum Mol Genet, 15 Spec No 1, R17-29.

Oda et al. (2009) High-resolution genome-wide cytosine methylation profiling with simultaneous copy number analysis and optimization for limited cell numbers. Nucleic Acids Res, 37, 3829-3839.

Orlowski and Bujnicki (2008) Structural and evolutionary classification of Type II restriction enzymes based on theoretical and experimental analyses. *Nucleic Acids Res*, 36, 3552-3569.

Reik (2007) Stability and flexibility of epigenetic gene regulation in mammalian development. *Nature*, 447, 425-432.

Riggs (1975) X inactivation, differentiation, and DNA methylation. *Cytogenet Cell Genet*, 14, 9-25.

Robertson and Wolffe (2000) DNA methylation in health and disease. *Nat Rev Genet*, 1, 11-19.

Suzuki and Bird (2008) DNA methylation landscapes: provocative insights from epigenomics. *Nat Rev Genet*, 9, 465-476.

Takamiya et al. (2009) The application of restriction landmark genome scanning method for surveillance of non-mendelian inheritance in f(1) hybrids. *Comp Funct Genomics*, 245927.

Vitkute et al. (2001) Specificities of eleven different DNA methyltransferases of *Helicobacter pylori* strain 26695. *J Bacteriol*, 183, 443-450.

Weber et al. (2005) Chromosome-wide and promoter-specific analyses identify sites of differential DNA methylation in normal and transformed human cells. *Nat Genet*, 37, 853-862.

Yan et al. (2002) Applications of CpG island microarrays for high-throughput analysis of DNA methylation. *J Nutr*, 132, 2430S-2434S.

Zheng et al. (2010) A unique family of Mrr-like modification-dependent restriction endonucleases. Nucleic Acids Res. 38: 5527-5534

While the invention has been illustrated by a description of various embodiments and while these embodiments have been described in detail, it is not Applicant's intention to restrict or in any way limit the scope of the appended claims to such detail. Additional advantages and modifications will readily appear to those skilled in the art. The invention in its broader aspects is therefore not limited to the specific details, representative enzymes, and methods, and illustrative examples shown and described. Accordingly, departures may be made from such details without departing from the spirit or scope of the claims.

Applicants incorporate by reference the material contained in the accompanying computer readable Sequence Listing identified as Sequence_Listing_ST25.txt, having a file creation date of Jun. 25, 2013, 2:06 p.m. and file size of 40.0 KB.

What is claimed is:

1. A method for determining the level of methylation in eukaryotic double stranded DNA, the method comprising
contacting a first sample of the eukaryotic double stranded DNA with a restriction endonuclease comprising SEQ ID NO. 4 or a sequence at least 70% identical to SEQ ID NO. 4, having a recognition sequence 5'-TCGA-3' where a modified cytosine residue in the recognition sequence impairs cleavage,
digesting the DNA comprising the recognition sequence 5'-TCGA-3' in which the cytosine residue is unmodified; and
determining the amount of undigested DNA or digested DNA.

2. The method of claim 1 further comprising
contacting a second sample of the double stranded DNA with a second restriction endonuclease; and
determining the amount of DNA digestion,
where the second restriction endonuclease has a recognition sequence 5'-TCGA-3' and is not impaired by modification of the cytosine residue.

3. The method of claim 1 wherein the eukaryotic double stranded DNA is genomic DNA.

4. The method of claim 1 wherein the amount of undigested DNA is determined using qPCR.

5. The method of claim 2 where the second restriction endonuclease is TaqI.

6. The method of claim 1 wherein the impaired ability to cleave the recognition sequence means that under conditions at which the restriction endonuclease is most active, optimal reaction conditions, the presence of the modified cytosine residue in the recognition sequence reduces the endonuclease's ability to cleave the sequence by more than 80%.

7. The method of claim 6 wherein the presence of the modified cytosine residue in the recognition sequence reduces the endonuclease's ability to cleave the sequence by more than 90%.

8. The method of claim 6 wherein the percent of DNA cleavage is determined by qPCR analysis.

9. The method of claim 1 wherein the modified cytosine residue is a methylated cytosine.

10. The method of claim 9 wherein the methylated cytosine is selected from the group consisting of 5-methylcytosine, 5-hydroxymethylcytosine, and glycosylated 5-hydroxymethylcytosine.

* * * * *